(12) United States Patent
Tunev et al.

(10) Patent No.: US 10,342,592 B2
(45) Date of Patent: Jul. 9, 2019

(54) SELECTIVE MODULATION OF RENAL NERVES

(71) Applicants: MEDTRONIC ARDIAN LUXEMBOURG SARL, Luxembourg (LU); Stefan Tunev, Santa Rosa, CA (US)

(72) Inventors: Stefan Tunev, Santa Rosa, CA (US); Julie Trudel, Santa Rosa, CA (US)

(73) Assignee: Medtronic Ardian Luxembourg S.A.R.L., Luxembourg (LU)

( * ) Notice: Subject to any disclaimer, the term of this patent is extended or adjusted under 35 U.S.C. 154(b) by 771 days.

(21) Appl. No.: 14/379,834

(22) PCT Filed: Mar. 7, 2013

(86) PCT No.: PCT/US2013/029526
§ 371 (c)(1),
(2) Date: Aug. 20, 2014

(87) PCT Pub. No.: WO2013/134469
PCT Pub. Date: Sep. 12, 2013

(65) Prior Publication Data
US 2015/0133850 A1 May 14, 2015

Related U.S. Application Data

(60) Provisional application No. 61/608,022, filed on Mar. 7, 2012.

(51) Int. Cl.
*A61B 18/00* (2006.01)
*A61B 18/04* (2006.01)
(Continued)

(52) U.S. Cl.
CPC .............. *A61B 18/04* (2013.01); *A61B 18/02* (2013.01); *A61B 18/1492* (2013.01);
(Continued)

(58) Field of Classification Search
CPC ..... A61B 18/04; A61B 18/02; A61B 18/0206; A61B 18/1492; A61B 18/18;
(Continued)

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

WO WO-199407446 4/1994
WO WO-1995025472 9/1995
(Continued)

OTHER PUBLICATIONS

U.S. Appl. No. 95/002,110, filed Aug. 29, 2012, Demarais et al.
(Continued)

*Primary Examiner* — Jason E Flick
*Assistant Examiner* — Courtney B Fredrickson

(57) ABSTRACT

Methods for treating a patient using therapeutic renal neuromodulation and associated devices, systems, and methods are disclosed herein. One aspect of the present technology is directed to methods including selectively neuromodulating afferent or efferent renal nerves. One or more measurable physiological parameters corresponding to systemic sympathetic overactivity or hyperactivity in the patient can thereby be reduced. Selectively neuromodulating afferent renal nerves can include inhibiting sympathetic neural activity in nerves proximate a renal pelvis. This can include, for example, neuromodulating via fluid within the renal pelvis. Selectively neuromodulating efferent renal nerves can include inhibiting sympathetic neural activity in nerves proximate a portion of a renal artery or a renal branch artery proximate a renal parenchyma. This can include, for
(Continued)

example, neuromodulating via a therapeutic element within the portion of the renal artery or the renal branch artery.

8 Claims, 10 Drawing Sheets

(51) Int. Cl.
| | |
|---|---|
| *A61N 1/05* | (2006.01) |
| *A61N 1/36* | (2006.01) |
| *A61B 18/02* | (2006.01) |
| *A61B 18/14* | (2006.01) |
| *A61B 18/18* | (2006.01) |
| *A61M 25/00* | (2006.01) |
| *A61N 1/32* | (2006.01) |
| *A61N 7/00* | (2006.01) |

(52) U.S. Cl.
CPC ..... *A61B 18/1815* (2013.01); *A61M 25/0084* (2013.01); *A61N 1/0551* (2013.01); *A61N 1/327* (2013.01); *A61N 1/3605* (2013.01); *A61N 7/00* (2013.01); *A61B 2018/00434* (2013.01); *A61B 2018/046* (2013.01); *A61M 2025/0089* (2013.01); *A61M 2202/048* (2013.01); *A61M 2202/049* (2013.01); *A61N 2007/003* (2013.01)

(58) Field of Classification Search
CPC .. A61B 2018/1861; A61B 2018/00434; A61B 2018/00505; A61B 2018/00511; A61N 1/3605; A61N 1/36057
See application file for complete search history.

(56) References Cited

U.S. PATENT DOCUMENTS

| | | | |
|---|---|---|---|
| 4,709,698 A | 12/1987 | Johnston et al. | |
| 4,764,504 A | 8/1988 | Johnson et al. | |
| 4,890,623 A | 1/1990 | Cook et al. | |
| 4,976,711 A | 12/1990 | Parins et al. | |
| 5,222,938 A * | 6/1993 | Behl | A61B 18/082 604/113 |
| 5,300,068 A | 4/1994 | Rosar et al. | |
| 5,358,514 A | 10/1994 | Schulman et al. | |
| 5,368,591 A | 11/1994 | Lennox et al. | |
| 5,423,744 A | 6/1995 | Gencheff et al. | |
| 5,425,364 A | 6/1995 | Imran | |
| 5,484,400 A | 1/1996 | Edwards et al. | |
| 5,571,147 A | 11/1996 | Sluijter et al. | |
| 5,588,964 A | 12/1996 | Imran et al. | |
| 5,599,345 A | 2/1997 | Edwards et al. | |
| 5,626,576 A | 5/1997 | Janssen | |
| 5,672,174 A | 9/1997 | Gough et al. | |
| 5,688,266 A | 11/1997 | Edwards et al. | |
| 5,700,282 A | 12/1997 | Zabara | |
| 5,707,400 A | 1/1998 | Terry, Jr. et al. | |
| 5,772,590 A | 6/1998 | Webster, Jr. | |
| 5,860,974 A * | 1/1999 | Abele | A61B 8/12 600/374 |
| 5,865,787 A | 2/1999 | Shapland et al. | |
| 5,893,885 A | 4/1999 | Webster et al. | |
| 5,944,710 A | 8/1999 | Dev et al. | |
| 5,954,719 A | 9/1999 | Chen et al. | |
| 5,983,141 A | 11/1999 | Sluijter et al. | |
| 6,004,269 A | 12/1999 | Crowley et al. | |
| 6,009,877 A | 1/2000 | Edwards | |
| 6,024,740 A | 2/2000 | Lesh et al. | |
| 6,036,687 A | 3/2000 | Laufer et al. | |
| 6,066,134 A | 5/2000 | Eggers et al. | |
| 6,091,995 A | 7/2000 | Ingle et al. | |
| 6,099,524 A | 8/2000 | Lipson et al. | |
| 6,117,101 A | 9/2000 | Diederich et al. | |
| 6,135,999 A | 10/2000 | Fanton et al. | |
| 6,149,620 A | 11/2000 | Baker et al. | |
| 6,161,048 A | 12/2000 | Sluijter et al. | |
| 6,219,577 B1 | 4/2001 | Brown, III et al. | |
| 6,224,592 B1 | 5/2001 | Eggers et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,292,695 B1 | 9/2001 | Webster, Jr. et al. | |
| 6,314,325 B1 | 11/2001 | Fitz | |
| 6,322,558 B1 | 11/2001 | Taylor et al. | |
| 6,322,559 B1 | 11/2001 | Daulton et al. | |
| 6,405,732 B1 | 6/2002 | Edwards et al. | |
| 6,413,255 B1 | 7/2002 | Stern | |
| 6,488,679 B1 | 12/2002 | Swanson et al. | |
| 6,506,189 B1 | 1/2003 | Rittman, III et al. | |
| 6,514,226 B1 | 2/2003 | Levin et al. | |
| 6,522,926 B1 | 2/2003 | Kieval et al. | |
| 6,542,781 B1 | 4/2003 | Koblish et al. | |
| 6,562,034 B2 | 5/2003 | Edwards et al. | |
| 6,616,624 B1 | 9/2003 | Kieval | |
| 6,622,731 B2 | 9/2003 | Daniel et al. | |
| 6,635,054 B2 | 10/2003 | Fjield et al. | |
| 6,685,648 B2 | 2/2004 | Flaherty et al. | |
| 6,711,444 B2 | 3/2004 | Koblish | |
| 6,736,835 B2 | 5/2004 | Pellegrino et al. | |
| 6,752,805 B2 | 6/2004 | Maguire et al. | |
| 6,845,267 B2 | 1/2005 | Harrison et al. | |
| 6,850,801 B2 | 2/2005 | Kieval et al. | |
| 6,869,431 B2 | 3/2005 | Maguire et al. | |
| 6,885,888 B2 | 4/2005 | Rezai | |
| 6,893,436 B2 | 5/2005 | Woodard et al. | |
| 6,939,346 B2 | 9/2005 | Kannenberg et al. | |
| 7,087,040 B2 * | 8/2006 | McGuckin, Jr. | A61B 18/00 604/158 |
| 7,149,574 B2 | 12/2006 | Yun et al. | |
| 7,162,303 B2 | 1/2007 | Levin et al. | |
| 7,217,245 B1 * | 5/2007 | Snow | A61B 5/015 600/407 |
| 7,221,979 B2 | 5/2007 | Zhou et al. | |
| 7,381,200 B2 | 6/2008 | Katoh et al. | |
| 7,390,894 B2 | 6/2008 | Weinshilboum et al. | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,778,703 B2 | 8/2010 | Gross et al. | |
| 8,131,371 B2 | 3/2012 | Demarais et al. | |
| 8,131,372 B2 | 3/2012 | Levin et al. | |
| 8,140,170 B2 | 3/2012 | Rezai et al. | |
| 8,145,317 B2 | 3/2012 | Demarais et al. | |
| 8,150,518 B2 | 4/2012 | Levin et al. | |
| 8,150,519 B2 | 4/2012 | Demarais et al. | |
| 8,150,520 B2 | 4/2012 | Demarais et al. | |
| 8,175,711 B2 | 5/2012 | Demarais et al. | |
| 2001/0056256 A1 * | 12/2001 | Hughes | A61M 5/007 604/85 |
| 2002/0087208 A1 | 7/2002 | Koblish et al. | |
| 2002/0107515 A1 | 8/2002 | Edwards et al. | |
| 2002/0139379 A1 | 10/2002 | Edwards et al. | |
| 2002/0165532 A1 | 11/2002 | Hill et al. | |
| 2002/0183682 A1 | 12/2002 | Darvish et al. | |
| 2003/0050635 A1 | 3/2003 | Truckai et al. | |
| 2003/0050681 A1 | 3/2003 | Pianca et al. | |
| 2003/0060858 A1 | 3/2003 | Kieval et al. | |
| 2003/0074039 A1 | 4/2003 | Puskas | |
| 2003/0125790 A1 | 7/2003 | Fastovsky et al. | |
| 2003/0181897 A1 | 9/2003 | Thomas et al. | |
| 2003/0195507 A1 | 10/2003 | Stewart et al. | |
| 2003/0199863 A1 | 10/2003 | Swanson et al. | |
| 2003/0216792 A1 | 11/2003 | Levin et al. | |
| 2003/0233099 A1 | 12/2003 | Danaek et al. | |
| 2004/0010289 A1 | 1/2004 | Biggs et al. | |
| 2004/0167509 A1 | 8/2004 | Taimisto | |
| 2004/0215186 A1 | 10/2004 | Cornelius et al. | |
| 2005/0004567 A1 * | 1/2005 | Daniel | A61B 18/1477 606/50 |
| 2005/0080409 A1 | 4/2005 | Young et al. | |
| 2005/0187579 A1 | 8/2005 | Danek et al. | |

(56) References Cited

U.S. PATENT DOCUMENTS

| | | |
|---|---|---|
| 2005/0228460 A1 | 10/2005 | Levin et al. |
| 2005/0288730 A1 | 12/2005 | Deem et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0212076 A1 | 9/2006 | Demarais et al. |
| 2006/0271111 A1 | 11/2006 | Demarais et al. |
| 2007/0129720 A1 | 6/2007 | Demarais et al. |
| 2007/0129760 A1* | 6/2007 | Demarais ............ A61B 18/1492 607/2 |
| 2007/0225564 A1* | 9/2007 | Couvillon, Jr. ........ A61B 1/012 600/140 |
| 2007/0265687 A1 | 11/2007 | Deem et al. |
| 2008/0319513 A1 | 12/2008 | Pu et al. |
| 2009/0036948 A1 | 2/2009 | Levin et al. |
| 2009/0118729 A1* | 5/2009 | Auth ................ A61B 18/1492 606/42 |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0112400 A1* | 5/2011 | Emery .................. A61B 8/12 600/439 |
| 2011/0172528 A1 | 7/2011 | Gertner |
| 2011/0208175 A1 | 8/2011 | Sobotka et al. |
| 2011/0264075 A1 | 10/2011 | Leung et al. |
| 2011/0264086 A1 | 10/2011 | Ingle |
| 2012/0101490 A1* | 4/2012 | Smith ................ A61B 17/3203 606/33 |
| 2012/0130289 A1 | 5/2012 | Demarais et al. |
| 2012/0130345 A1 | 5/2012 | Levin et al. |
| 2012/0172837 A1 | 7/2012 | Demarais et al. |
| 2013/0053732 A1 | 2/2013 | Heuser |

FOREIGN PATENT DOCUMENTS

| | | |
|---|---|---|
| WO | WO-9531142 | 11/1995 |
| WO | WO-1997036548 | 10/1997 |
| WO | WO-1999/00060 | 1/1999 |
| WO | WO-2001022897 | 4/2001 |
| WO | WO-2001070114 | 9/2001 |
| WO | WO-2003022167 | 3/2003 |
| WO | WO-2003/082080 | 10/2003 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO-2006105121 | 10/2006 |
| WO | WO-2007008954 | 1/2007 |
| WO | WO-2007078997 | 7/2007 |
| WO | WO-2008049084 | 4/2008 |
| WO | WO-2010/067360 | 6/2010 |
| WO | WO-2013/010009 | 1/2013 |
| WO | WO-2013/134469 | 9/2013 |

OTHER PUBLICATIONS

U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heartorg/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news—latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.I.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty For The Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul lntegr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013,

(56) References Cited

OTHER PUBLICATIONS 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Dubuc, M., et al., "Feasibility of cardiac cryoablation using a transvenous steerable electrode catheter." J Intery Cardiac Electrophysiol, 2:285-292 (1998).

Final Office Action; U.S. Appl. No. 12/827,700; dated Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet The Tech Duo That's Revitalizing The Medical Device Industry." FAST COMPANY, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." Am. J. Roentgenol,174: 1592-1594 (2000).

Han, Y.-M, et al., "Renal artery ebolization with diluted hot contrast medium: An experimental study." J Vasc Intery Radiol, 12: 862-868 (2001).

Hansen, J. M., et al. "The transplanted human kidney does not achieve functional reinnervation." Clin. Sci, 87: 13-19 (1994).

Hendee, W. R. et al. "Use of Animals in Biomedical Research: The Challenge and Response." American Medical Association White Paper (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter ablation of cardiac autonomic nerves for prevention of vagal atrial fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Solis-Herruzo et al., "Effects of lumbar sympathetic block on kidney function in cirrhotic patients with hepatorenal syndrome," J. Hepatol. 5 (1987), pp. 167-173.

Stella, A., et al., "Effects of reversible renal denervation on haemodynamic and excretory functions on the ipsilateral and contralateral kidney in the cat." Hypertension, 4:181-188 (1986).

Stouffer, G. A. et al., "Catheter-based renal denervation in the treatment of resistant hypertension." Journal of Molecular and Cellular Cardiology, vol. 62, 2013, 6 pages.

Swartz, J.F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Weinstock, M., et al., "Renal denervation prevents sodium retention and hypertension in salt sensitive rabbits with genetic baroreflex impairment." Clinical Science, 90:287-293 (1996).

(56) References Cited

OTHER PUBLICATIONS

Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding A Future For Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Kru M, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
International Search Report and Written Opinion for International App. No. PCT/US13/29526, dated Jun. 5, 2013, 9 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.

(56) References Cited

OTHER PUBLICATIONS

Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.com/time/printout/08,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
European Search Report for European Application No. 13159256, dated Oct. 17, 2013, 6 pages.
U.S. Appl. No. 60/852,787, filed Oct. 18, 2006, 112 pages.

Pieper et al., "Design and Implementation of a New Computerized System for Intraoperative Cardiac Mapping." Journal of Applied Physiology, 1991, vol. 71, No. 4, pp. 1529-1539.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
Kumagai, H. et al., "Importance of rostral ventrolateral medulla neurons in determining efferent sympathetic nerve activity and blood pressure." Hypertension Research 2011, 10 pages.
Stella, A. et al., "Functional Role of Renal Afferents." Physiological Reviews, vol. 71, No. 3, Jul. 1991, 24 pages.
Katholi, K. et al., "The Role of Renal Sympathetic Nerves in Hypertension: Has Percutaneous Renal Denervation Refocused Attention on Their Clinical Significance?" Progress in Cardiovascular Disease 52, 2009, 6 pages.
Kopp, U., et al., "Activation of EP4 receptors contributes to prostaglandin E 2-mediated stimulation of renal sensory nerves." Am J. Physiol Renal Physiol 287, 2004, 15 pages.
Rousselle, S., "Experimental Pathways for the Evaluation of Extrinsic Renal Nerve Distribution, Density, and Quantification (Swine Model)", Cancer Research Foundation, Nov. 8, 2011, 20 pages.
Supplementary European Search Report for European Patent Application No. EP13758601; dated Oct. 6, 2015; 9 pages.
Schlaich, Markus P., et al., "Renal Sympathetic Nerve Ablation: The New Frontier in the Treatment of Hypertension", Curr Hypertens Rep (2010) 12:39-46, Jan. 16, 2010, Springer Science+Business Media, LLC, US.
Krum, et al., "Catheter-Based Renal Sympathetic Denervation for Resistant Hypertension Durability of Blood Pressure Reduction Out to 24 Months" Hypertension, 2011, vol. 57, pp. 911-917.
"Peregrine System—Peregrine System Procedure." Ablative Solutions, 2015, 2 pages, http://ablativesolutions.com/us.about-hypertension/> (accessed Mar. 22, 2016).
"Bullfrog Micro-Infusion Device." Mercator MedSystems, 2016, 2 pages, http://www.mercatormed.com/bullfrog-micro-infusion-device/> (accessed Mar. 22, 2016).

* cited by examiner

*Arterial Vasculature*

*Venous Vasculature*

SELECTIVE MODULATION OF RENAL NERVES

CROSS-REFERENCE TO RELATED APPLICATION(S)

The present application claims priority to U.S. Provisional Patent Application No. 61/608,022, filed Mar. 7, 2012, entitled "SELECTIVE MODULATION OF RENAL NERVES," which is incorporated herein in its entirety by reference.

TECHNICAL FIELD

The present technology relates generally to the modulation of renal nerves. In particular, several embodiments are directed to the selective modulation of renal nerves, e.g., the selective modulation of afferent renal nerves over efferent renal nerves and the selective modulation of efferent renal nerves over afferent renal nerves.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine spillover rates in patients with essential hypertension.

Sympathetic nerves of the kidneys terminate in the blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, i.e., renal dysfunction as a progressive complication of chronic heart failure. Pharmacologic strategies to thwart the consequences of renal sympathetic stimulation include centrally-acting sympatholytic drugs, beta blockers (intended to reduce renin release), angiotensin-converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1:
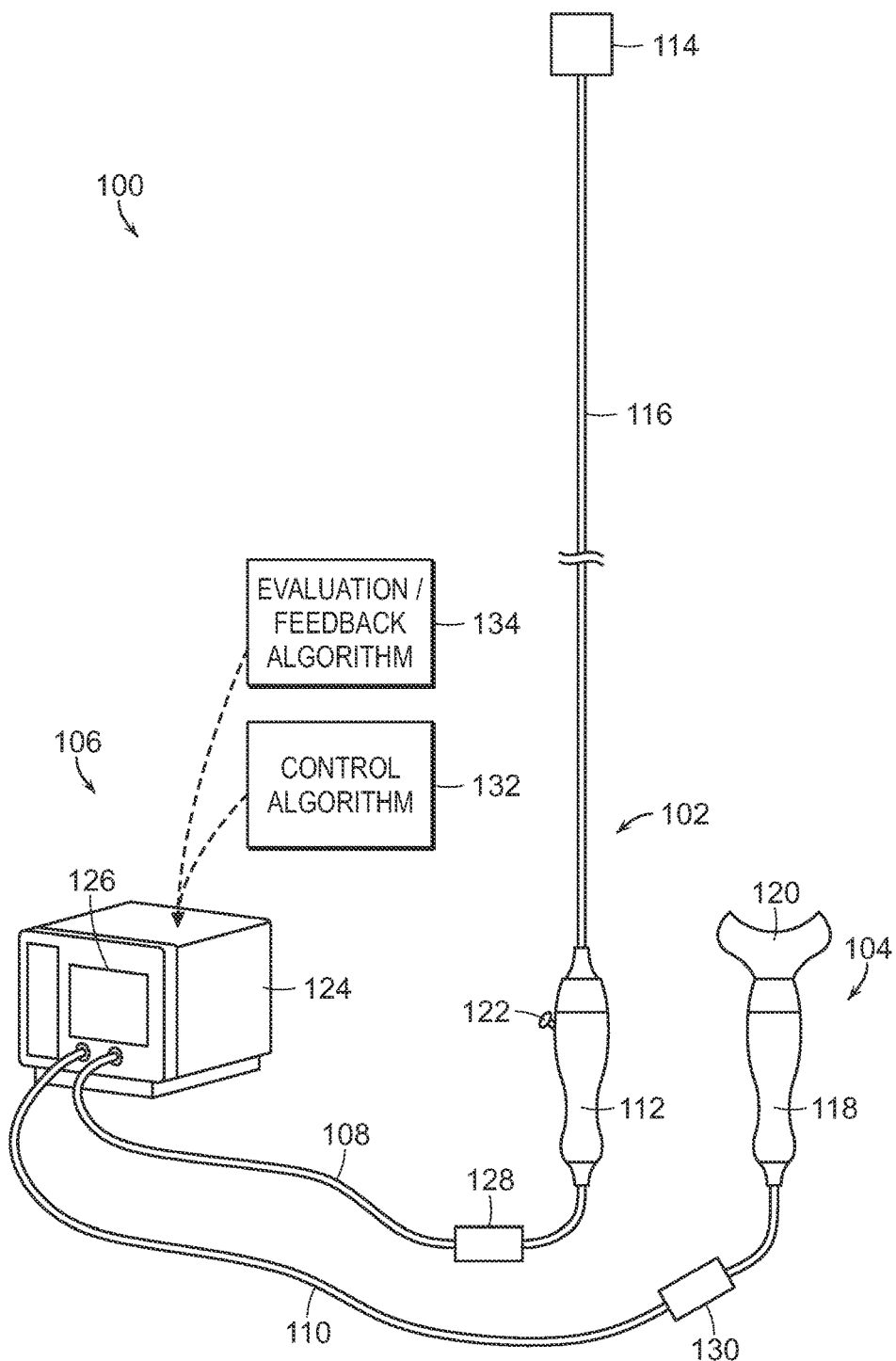
FIG. 1 is a partially-schematic view illustrating a renal neuromodulation system configured in accordance with an embodiment of the present technology.

The present technology is generally directed to the selective modulation of renal nerves. Specific details of several embodiments of the present technology are described herein with reference to FIGS. 1-12B. Although many of the embodiments are described herein with respect to devices, systems, and methods for modulation of renal nerves using electrically-induced, thermally-induced, and chemically-induced approaches, other applications and other treatment modalities in addition to those described herein are within the scope of the present technology. Additionally, other embodiments of the present technology can have different configurations, components, or procedures than those described herein. For example, other embodiments can include additional elements and features beyond those described herein or be without several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically-numbered parts are distinct in structure and/or function.

Generally, unless the context indicates otherwise, the terms "distal" and "proximal" within this disclosure reference a position relative to an operator or an operator's control device. For example, "proximal" can refer to a position closer to an operator or an operator's control device, and "distal" can refer to a position that is more distant from an operator or an operator's control device. The headings provided herein are for convenience only.

I. Renal Neuromodulation

Renal neuromodulation is the partial or complete incapacitation or other effective disruption of nerves innervating the kidneys, e.g., nerves terminating in or originating from a kidney or in structures closely associated with a kidney. In particular, renal neuromodulation can include inhibiting, reducing, and/or blocking neural communication along neural fibers (e.g., efferent and/or afferent neural fibers) innervating the kidneys. Such incapacitation can be long-term (e.g., permanent or for periods of months, years, or decades) or short-term (e.g., for periods of minutes, hours, days, or weeks). While long-term disruption of the renal nerves can be desirable for alleviating symptoms and other sequelae associated with central sympathetic overstimulation over longer periods of time, short-term modulation of the renal nerves may also be desirable. For example, some patients may benefit from short-term modulation to address issues relating to an acute stage of fluid retention or heart failure.

As described in greater detail below with reference to FIGS. 9-12B, sympathetic nerves (e.g., efferent and/or afferent neural fibers) can contribute to a number of cardiovascular-related diseases and conditions (e.g., hypertension, heart failure, left ventricular hypertrophy, cardio-renal syndrome, etc.), metabolic-related diseases and conditions (metabolic syndrome, insulin resistance, diabetes, etc.), endocrine-related diseases and conditions (e.g., polycystic ovary syndrome, osteoporosis, erectile dysfunction, etc.) among others. For example, obesity and hypertension can be characterized by increased efferent sympathetic drive to the kidneys and increased systemic sympathetic nerve firing modulated by afferent signaling from renal sensory nerves. The role of renal sympathetic nerves as contributors to the pathogenesis of elevated blood pressure, particularly in obese patients, has been demonstrated both experimentally and in humans. Apart from its role in cardiovascular regulation, sympathetic nervous system activation also has metabolic effects resulting in increased lipolysis and increased levels of fatty acids in plasma, increased hepatic gluconeogenesis, and alterations in pancreatic insulin release. Chronic sympathetic activation predisposes to the development of insulin resistance, which is often associated with obesity and hypertension which can also be a key feature of many endocrine-related conditions (e.g., polycystic ovary syndrome, erectile dysfunction, etc.).

Renal neuromodulation can contribute to the systemic reduction of sympathetic tone or drive. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions. Furthermore, renal neuromodulation can potentially benefit a variety of organs and bodily structures innervated by sympathetic nerves.

Several properties of the renal vasculature may inform the design of treatment devices and associated methods for achieving selective renal neuromodulation, for example, via intravascular access, and impose specific design requirements for such devices. Specific design requirements may include accessing the renal artery, a ureter, a renal pelvis, a major renal calyx, a minor renal calyx, and/or another suitable structure; facilitating stable contact between the energy delivery elements of such devices and a luminal surface or wall of the suitable targeted structure, and/or effectively and selectively modulating the renal nerves with the neuromodulatory apparatus.

II. Selected Examples of Neuromodulation Modalities

Various techniques can be used to partially or completely incapacitate neural pathways, such as those innervating the kidney. Renal neuromodulation, in accordance with embodiments of the present technology, can be electrically-induced, thermally-induced, chemically-induced, or induced in another suitable manner or combination of manners at one or more suitable treatment locations during a treatment procedure. For example, the purposeful application of radiofrequency (RF) energy (monopolar and/or bipolar), pulsed RF energy, microwave energy, optical energy, ultrasound energy (e.g., delivered by catheter, extracorporeal, high-intensity focused ultrasound (HIFU)), cryotherapeutic energy, direct heat energy, radiation (e.g., infrared, visible, gamma), chemicals (e.g., drugs or other agents), or combinations thereof to tissue at a treatment location can induce one or more desired effects at the treatment location, e.g., broadly across the treatment location or at localized regions of the treatment location. The treatment location can be proximate (e.g., at or near) a vessel or chamber wall (e.g., a wall of a renal artery, a ureter, a renal pelvis, a major renal calyx, a minor renal calyx, and/or another suitable structure), and the treated tissue can include tissue proximate the treatment location. For example, with regard to a renal artery, a treatment procedure can include modulating nerves in the renal plexus, which lay intimately within or adjacent to the adventitia of the renal artery.

In some embodiments, the purposeful application of energy (e.g., electrical energy, thermal energy, etc.) to tissue can induce one or more desired thermal heating and/or cooling effects on localized region of the renal artery or other target tissue (e.g., a ureter, a renal pelvis, a major renal calyx, a minor renal calyx, and/or another suitable structure). Some embodiments of the present technology, for example, include cooling tissue at a target site in a manner that modulates neural function. Accordingly, renal neuromodulation can include a cryotherapeutic treatment modality alone or in combination with another treatment modality. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death, e.g., during tissue thawing and subsequent hyperperfusion. Neuromodulation using a cryotherapeutic treatment in accordance with embodiments of the present technology can include cooling a structure proximate (e.g., adjacent) an inner surface of a vessel or chamber wall such that tissue is effectively cooled to a depth where sympathetic renal nerves reside. For example, a cooling assembly of a cryotherapeutic device can be cooled to the extent that it causes therapeutically-effective, cryogenic renal neuromodulation. In some embodiments, a cryotherapeutic treatment modality can include cooling that is not configured to cause neuromodulation. For example, the cooling can be at or above cryogenic temperatures and can be used to control neuromodulation via another treatment modality, e.g., to reduce damage to non-targeted tissue when targeted tissue adjacent to the non-targeted tissue is heated.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause the kidneys to rise and fall and thereby move the renal arteries and other structures associated with the kidneys. In addition, blood flow is pulsatile and can cause structures associated with the kidneys to pulse. Cryogenic adhesion also can facilitate intravascular or intraluminal positioning, particularly in relatively-small structures (e.g., relatively-short arteries) in which stable intravascular or intraluminal positioning can be difficult to achieve.

As an alternative to or in conjunction with cryotherapeutic cooling, other suitable energy delivery techniques, such as electrode-based or transducer-based approaches, can be used for therapeutically-effective and selective renal neuromodulation. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. As noted previously, suitable energy modalities can include, for example, RF energy (monopolar and/or bipolar), pulsed RF energy, microwave energy, ultrasound energy (e.g., intravascularly delivered ultrasound, extracorporeal ultrasound, HIFU), laser energy, optical energy, magnetic energy, direct heat, radiation (e.g., infrared, visible, gamma), or other suitable energy modalities alone or in combination. Where a system uses a monopolar configuration, a return electrode or ground patch fixed externally on the subject can be used. Moreover, electrodes (or transducers or other energy delivery elements) can be used alone or with other electrodes or transducers in a multi-electrode or multi-transducer array. Examples of suitable multi-electrode devices are described in U.S. patent application Ser. No. 13/281,360, filed Oct. 25, 2011, and incorporated herein by reference in its entirety. Other suitable devices and technologies, such as cryotherapeutic devices, are described in U.S. patent application Ser. No. 13/279,330, filed Oct. 23, 2011, and additional thermal devices are described in U.S. patent application Ser. No. 13/279,205, filed Oct. 21, 2011, each of which are incorporated herein by reference in their entireties. Furthermore, the energy can be applied from within the body (e.g., within the vasculature or other body lumens in a catheter-based approach) and/or from outside the body, e.g., via an applicator positioned outside the body. In some embodiments, energy can be used to reduce damage to non-targeted tissue when targeted tissue adjacent to the non-targeted tissue is subjected to neuromodulating cooling.

Ultrasound energy (e.g., HIFU energy) can be beneficial in certain embodiments. Focused ultrasound is an example of a transducer-based treatment modality that can be delivered from outside the body. In some embodiments, focused ultrasound treatment can be performed in close association with imaging, e.g., magnetic resonance, computed tomography, fluoroscopy, ultrasound (e.g., intravascular or intraluminal), optical coherence tomography, or another suitable imaging modality. For example, imaging can be used to identify an anatomical position of a treatment location, e.g., as a set of coordinates relative to a reference point. The coordinates can then entered into a focused ultrasound device configured to change the power, angle, phase, or other suitable parameters to generate an ultrasound focal zone at the location corresponding to the coordinates. In some embodiments, the focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Thermal effects of neuromodulation treatment can include both ablation and non-ablative thermal alteration or damage, (e.g., via sustained heating and/or resistive heating) to partially or completely disrupt the ability of a nerve to transmit a signal. Desired thermal heating effects, for example, can include raising the temperature of target neural fibers to a desired target temperature above a first threshold to achieve non-ablative alteration, or above a second, higher threshold to achieve ablative thermal alteration. In some embodiments, the target temperature can be higher than about body temperature (e.g., about 37° C.) but less than about 45° C. for non-ablative thermal alteration, and the target temperature can be higher than about 45° C. for ablative thermal alteration. More specifically, exposure to thermal energy in excess of a body temperature of about 37° C., but below a temperature of about 45° C., may induce thermal non-ablative alteration, for example, via moderate heating of target neural fibers or of vascular or luminal structures that perfuse the target neural fibers. In cases where vascular structures are affected, the target neural fibers may be denied perfusion resulting in necrosis of the neural tissue. For example, this may induce non-ablative thermal alteration in the fibers or structures. Exposure to heat above a temperature of about 45° C., or above (e.g., higher than about 60° C.), may induce thermal alteration via substantial heating of the fibers or structures. For example, such higher temperatures may thermally ablate the target neural fibers or of vascular or luminal structures that perfuse the target fibers. In some patients, it can be desirable to heat tissue to temperatures that are sufficient to thermally ablate the target neural fibers or the vascular or luminal structures, but that are less than about 90° C., or are less than about 85° C., or less than about 80° C., and/or less than about 75° C. Other embodiments can include heating tissue to a variety of other suitable temperatures.

In some embodiments, renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. In some embodiments, the chemical can be guanethidine, ethanol, phenol, vincristine, a neurotoxin, or another suitable agent selected to alter, damage, or disrupt nerves. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more devices, such as needles originating outside the body or within the vasculature or other body lumens or delivery pumps (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., micro-needles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

III. Selective Renal Neuromodulation

The kidneys are innervated with both afferent and efferent nerves. As a sensory organ, the kidney comprises both chemoreceptors and baroreceptors that are connected with the central nervous system via afferent nerve fibers, which can then regulate blood pressure and central sympathetic outflow. The efferent renal nerves carry signals from the central nervous system to the kidneys. Afferent and efferent renal nerves can affect the progression of disease states (e.g., hypertension) associated with systemic sympathetic overactivity or hyperactivity in different ways. For example, activation of renal efferent nerves can increase sodium reabsorption/retention, increase renin release (and subsequent renin-angiotensin-aldosterone system (RAAS) activation), and decrease renal blood flow, all of which can have effects on central sympathetic drive such as increasing blood pressure. As discussed above, renal sensory afferent nerves can stimulate the hypothalamus to increase systemic sympathetic discharge (e.g., activate the centrally-mediated sympathetic nervous system). This direct systemic activation can have such consequences as increasing peripheral vascular resistance and increasing sympathetic drive to the heart (which increases heart rate and cardiac contractility), thereby increasing blood pressure.

Adverse consequences of chronic sympathetic overactivity, such as hypertension, left ventricular hypertrophy (LVH), ventricular arrhythmias, sudden cardiac death, insulin resistance, diabetes, metabolic syndrome among other endocrine disorders (e.g., polycystic ovary syndrome, erectile dysfunction, etc.) are documented both experimentally and in humans. While both efferent and afferent renal nerve fibers can contribute to central sympathetic drive including, for example, overactivity or hyperactivity of the central sympathetic system, there is evidence from studies of animal dorsal rhizotomy as well as human studies using direct recordings of muscle sympathetic nerve activity (MSNA) that sensory afferent signals originating from diseased or damaged kidneys are contributors to initiating and sustaining elevated central sympathetic outflow within this subject group. While the specific factors that bind and activate the renal nerves (e.g., at the site of these diseased or damaged kidneys) are not well understood, and without being bound by theory, it is thought that afferent renal nerve activation can be initiated by mechanoreceptor- and chemoreceptor-mediated secretion of adenosine in response to, for example, ischemia-induced hypoxia.

Positive outcomes have been reported from neuromodulation of both the afferent and efferent renal nerves. As evidenced by positive, long-term outcomes in kidney transplant patients, both afferent and efferent communication with the kidneys can be disabled in some cases without serious complications. Much of the functionality of efferent renal nerves, for example, can be redundant to other bodily systems. Accordingly, some approaches to renal neuromodulation can be non-selective with respect to afferent and efferent renal nerves. For example, modulation of a renal plexus via a renal artery (e.g., intravascular access) typically affects both afferent and efferent renal nerves. There can be reasons, however, to modulate afferent or efferent renal nerves selectively.

Selective renal neuromodulation can include modulating afferent renal nerves preferentially over efferent renal nerves or, in another embodiment, modulating efferent renal nerves preferentially over afferent renal nerves. Complete selectivity may not be necessary, but rather several embodiments include modulating one of the efferent or afferent renal nerves to a greater extent than the other. Kidneys typically include a greater number of efferent nerves than afferent nerves, so selective modulation of afferent renal nerves can still involve modulating a greater number of efferent renal nerves than afferent renal nerves in several embodiments. For example, a treatment procedure for selective modulation of afferent renal nerves can modulate a greater percentage of the total afferent renal nerves of a kidney and a lower percentage of the total efferent renal nerves of the kidney. Similarly, selective modulation of efferent renal nerves can modulate a greater percentage of the total efferent renal nerves of a kidney and a lower percentage of the total afferent renal nerves of the kidney. In some embodiments of treatment procedures in accordance with the present technology, selective modulation of afferent renal nerves can include modulating greater than about 50% (e.g., greater than about 60% or greater than about 70%) of the total afferent renal nerves of a kidney and less than about 50% (e.g., less than about 40% or less than about 30%) of the total efferent renal nerves of the kidney. Similarly, an embodiment of a treatment procedure for selective modulation of efferent renal nerves can include modulating greater than about 50% (e.g., greater than about 60% or greater than about 70%) of the total efferent renal nerves of a kidney and less than about 50% (e.g., less than about 40% or less than about 30%) of the total afferent renal nerves of the kidney.

In some cases, certain disease states can be associated with higher activity of afferent renal nerves compared to the activity of efferent renal nerves, while other disease states are associated with higher activity of efferent renal nerves than with the activity of afferent renal nerves. For example, selective modulation of one of afferent and efferent renal nerves can have a greater effect on some or all disease states associated with systemic sympathetic overactivity or hyperactivity than selective modulation of the other. In some cases, selective modulation of afferent renal nerves can have a greater effect on renal conditions (e.g., polycystic kidney disease) than selective modulation of efferent renal nerves. Furthermore, with respect to certain disease states, selective renal neuromodulation can provide some of, most of, all of, or more than the beneficial effect of non-selective renal neuromodulation. For example, selective modulation of afferent renal nerves may be therapeutically effective for the treatment of erectile dysfunction about equally or to a greater extent than non-selective renal neuromodulation.

Neuromodulation selective to one of the afferent or efferent renal nerves may, for example, cause less disruption of normal renal-nerve activity than non-selective renal neuromodulation. Preserving more functionality of one of the afferent or efferent renal nerves compared to non-selective renal neuromodulation can, in some instances, have specific utility. For example, preserving some or all renal afferent functionality may be useful to reduce the possibility of late detection of kidney stones that would otherwise have been detectable earlier due to a pain response carried by afferent renal nerves. This can be particularly useful in patients diagnosed as having cystinuria or as having an increased risk of developing kidney stones relative to the general population, e.g., based on a familial history of kidney stones. Preserving renal efferent functionality may be useful, for example, in some patients having an inability or a reduced ability to compensate for missing renal efferent functionality with other bodily systems.

Selective renal neuromodulation in accordance with embodiments of the present technology can include preferentially targeting one of the afferent or efferent renal nerves over the other based on their predominant anatomical positions. With respect to a single kidney, the renal plexus includes both afferent and efferent renal nerves toward the renal ostium where the renal artery meets the aorta. The majority of afferent renal nerves of the renal plexus, however, branch off renal-nerve bundles of the renal plexus before entering the renal parenchyma. These afferent renal nerves are mostly located and/or terminate along the renal pelvic wall. In contrast, most of the efferent renal nerves of the renal plexus continue into the renal parenchyma. With this anatomy in mind, a relatively-high concentration of afferent renal nerves can be found at the renal pelvis and a relatively-high concentration of efferent renal nerves can be found at the renal plexus near the renal parenchyma. Other locations having relatively-high concentrations of afferent or efferent renal nerves are also possible.

IV Selected Examples Of Renal Neuromodulation Systems

FIG. 1 is a partially-schematic diagram illustrating a renal neuromodulation system 100 that can include a first treatment device 102, a second treatment device 104, and an energy source or console 106. The system 100 can further include a first cable 108 extending between the console 106 and the first treatment device 102 and a second cable 110 extending between the console 106 and the second treatment device 104. The first and second treatment devices 102, 104 can be configured for different treatment modalities or different aspects of the same treatment modality. For example, the first treatment device 102 can be configured to perform or facilitate renal neuromodulation from within the vasculature or other body lumens and the second treatment device 104 can be configured to perform or facilitate renal neuromodulation from outside the body. In other embodiments, the system 100 can include only the first treatment device 102 or only the second treatment device 104. Furthermore, in some embodiments, rather than being a handheld device, the second treatment device 104 can be a stationary device mounted near a chair or bed on which a patient can be positioned. For example, the second treatment device 104 can be automatically positioned relative to the chair or bed based on entered coordinates.

As shown in FIG. 1, the first treatment device 102 can include a first handle 112, a therapeutic element 114, and an elongated shaft 116 extending between the first handle 112 and the therapeutic element 114. The second treatment device 104 can include a second handle 118 and a head 120. With regard to the first treatment device 102, the shaft 116 can be configured to locate the therapeutic element 114 intravascularly or in other body lumens (e.g., via a renal artery or a ureter) at a treatment location in or near a vessel or other body lumen associated with renal function, and the therapeutic element 114 can be configured to provide or support therapeutically-effective, renal neuromodulation at the treatment location. In some embodiments, the shaft 116 and the therapeutic element 114 can be 3, 4, 5, 6, or 7 French or another suitable size. Furthermore, the shaft 116 and the therapeutic element 114 can be partially or fully radiopaque and/or can include radiopaque markers corresponding to measurements, e.g., every 5 cm.

Intravascular delivery can include percutaneously inserting a guide wire (not shown) within the vasculature and moving the shaft 116 and the therapeutic element 114 along the guide wire until the therapeutic element 114 reaches the treatment location. For example, the shaft 116 and the therapeutic element 114 can include a guide-wire lumen (not shown) configured to receive the guide wire in an over-the-wire or rapid-exchange configuration. Other body lumens, such as ducts (e.g., a ureter) or internal chambers, can be treated by non-percutaneously passing the shaft 116 and therapeutic element 114 through externally accessible passages of the body. In some embodiments, a distal end of the therapeutic element 114 can terminate in an atraumatic rounded tip or cap (not shown). The first treatment device 102 can also be a steerable or non-steerable catheter device (e.g., a guide catheter) configured for use without a guide wire. Use of a guide wire, for example, is not included in some ureteric catheterization techniques.

The therapeutic element 114 can have a single state or configuration, or it can be convertible between a plurality of states or configurations. For example, the therapeutic element 114 can be configured to be delivered to a treatment location in a delivery state and to provide or support therapeutically-effective, renal neuromodulation in a deployed state. In these and other embodiments, the therapeutic element 114 can have different sizes and/or shapes in the delivery and deployed states. For example, the therapeutic element 114 can have a low-profile configuration in the delivery state and an expanded configuration in the deployed state. The therapeutic element 114 can be converted (e.g., placed or transformed) between the delivery and deployed states via remote actuation, e.g., using an actuator 122 of the first handle 112. The actuator 122 can include a knob, a pin, a lever, a button, a dial, or another suitable control component. In other embodiments, the therapeutic element 114 can be transformed between the delivery and deployed states using other suitable mechanisms or techniques.

The therapeutic element 114 can include an elongated member (not shown) that can be configured to curve (e.g., arch) in the deployed state, e.g., in response to movement of the actuator 122. For example, the elongated member can be at least partially helical/spiral in the deployed state. In other embodiments, the therapeutic element 114 can include a balloon (not shown) that can be configured to be at least partially inflated in the deployed state. An elongated member, for example, can be well suited for carrying one or more heating elements, electrodes or transducers and for delivering direct heat, electrode-based or transducer-based treatment. A balloon, for example, can be well suited for containing refrigerant (e.g., during or shortly after liquid-to-gas phase change) and for delivering cryotherapeutic treatment. A balloon can also be used in some embodiments for carrying suitable RF conducting electrodes. In some embodiments, the therapeutic element 114 can be configured for intravascular, transvascular, intraluminal, and/or transluminal delivery of chemicals. For example, the therapeutic element 114 can include one or more openings (not shown), and chemicals (e.g., drugs or other agents) can be deliverable through the openings. For transvascular or transluminal delivery, the therapeutic element 114 can include one or more needles (not shown) (e.g., retractable needles) and the openings can be at end portions of the needles.

The console 106 can be configured to control, monitor, supply, or otherwise support operation of the first and second treatment devices 102, 104. In some embodiments, the console 106 can be separate from and in communication with the first and/or second treatment devices 102, 104. In other embodiments, the console 106 can be contained within or be a component of the first and/or second treatment devices 102, 104. In still further embodiments, the console 106 can be configured for use with only one of the first and second treatment devices 102, 104 and the system 100 can include another console configured for use with the other of the first and second treatment devices 102, 104. In still other embodiments, the first treatment device 102 and/or the second treatment device 104 can be self-contained and/or otherwise configured for operation without connection to the console 106. As shown in FIG. 1, the console 106 can include a primary housing 124 having a display 126. The system 100 can include a first control device 128 along the first cable 108 and a second control device 130 along the second cable 110 configured, respectively, to initiate, terminate, and/or adjust operation of the first treatment device 102 and/or the second treatment device 104 directly and/or via the console 106. In other embodiments, the system 100 can include another suitable control mechanism. For example, the first control device 128 can be incorporated into the first handle 112 and/or the second control device 130 can be incorporated into the second handle 118.

The console 106 can be configured to execute an automated control algorithm 132 and/or to receive control instructions from an operator. Furthermore, the console 106 can be configured to provide feedback to an operator before, during, and/or after a treatment procedure via the display 126 and/or an evaluation/feedback algorithm 134. In some embodiments, the console 106 can include a processing device (not shown) having processing circuitry, e.g., a microprocessor. The processing device can be configured to execute stored instructions relating to the control algorithm 132 and/or the evaluation/feedback algorithm 134. Furthermore, the console 106 can be configured to communicate with the first and/or second treatment devices 102, 104, e.g., via the first and/or second cables 108, 110, respectively. For example, the therapeutic element 114 of the first treatment device 102 can include a sensor (not shown) (e.g., a temperature sensor, a pressure sensor, or a flow rate sensor) and a sensor lead (not shown) (e.g., an electrical lead or a pressure lead) configured to carry a signal from the sensor to the first handle 112. The first cable 108 can be configured to carry the signal from the first handle 112 to the console 106.

The console 106 can have different configurations depending on the treatment modalities of the first and second treatment devices 102, 104. For example, when one or both of the first and second treatment devices 102, 104 is configured for electrode-based or transducer-based treatment, the console 106 can include an energy generator (not shown) configured to generate RF energy, pulsed RF energy, microwave energy, optical energy, ultrasound energy (e.g., intravascularly delivered ultrasound, extracorporeal ultrasound, HIFU), magnetic energy, direct heat energy, or another suitable type of energy. In some embodiments, the console 106 can include an RF generator operably coupled to one or more electrodes (not shown) of the therapeutic element 114 of the first treatment device 102 and a focused-ultrasound generator operably coupled to one or more electrodes or transducers (not shown) of the head 120 of the second treatment device 104.

When the first treatment device 102 is configured for cryotherapeutic treatment, the console 106 can include a refrigerant reservoir (not shown) and can be configured to supply the first treatment device 102 with refrigerant, e.g., pressurized refrigerant in liquid or substantially liquid phase. Similarly, when the first treatment device 102 is configured for chemical-based treatment, the console 106 can include a chemical reservoir (not shown) and can be configured to supply the first treatment device 102 with the chemical. In some embodiments, the first treatment device 102 can include an adapter (not shown) (e.g., a luer lock) configured to be operably coupled to a syringe (not shown). The adapter can be fluidly connected to a lumen (not shown) of the treatment device 102, and the syringe can be used, for example, to manually deliver one or more chemicals to the treatment location, to withdraw material from the treatment location, to inflate a balloon (not shown) of the therapeutic element 114, to deflate a balloon of the therapeutic element 114, or for another suitable purpose.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration (e.g., a helical coil). Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

V. Selected Examples Of Treatment Procedures For Selective Modulation Of Afferent Renal Nerves Treatment procedures for selective modulation of afferent renal nerves in accordance with embodiments of the present technology can include applying a treatment modality at one or more treatment locations proximate a structure having a relatively-high concentration of afferent renal nerves and/or closer to afferent renal nerves than efferent renal nerves. In some embodiments, at least one treatment location can be proximate the renal pelvic anatomy of a kidney, which can include, for example, the renal pelvis, the ureteropelvic junction, the major calyces, the minor calyces, and/or other suitable structures. In general, the renal pelvic anatomy can have a larger and more irregular wall structure than the renal artery. Furthermore, nerve tissue can be shallower around the renal pelvic anatomy than around the renal artery. For example, a majority of afferent renal nerves at the renal pelvic anatomy can be within about 2 mm (e.g., about 1 mm) of the inside surface of the epithelium. In contrast, a majority of nerves in the renal plexus can be a greater distance from an inner surface of the renal artery. A therapeutic element of a treatment device can be positioned at a treatment location within the renal pelvic anatomy, for example, via a catheterization path including the urethra, the bladder, and the ureter, but other suitable catheterization paths may be used. Catheterization can be guided, for example, using imaging, e.g., magnetic resonance, computed tomography, fluoroscopy, ultrasound (e.g., intravascular or intraluminal), optical coherence tomography, or another suitable imaging modality.

Figure 2:
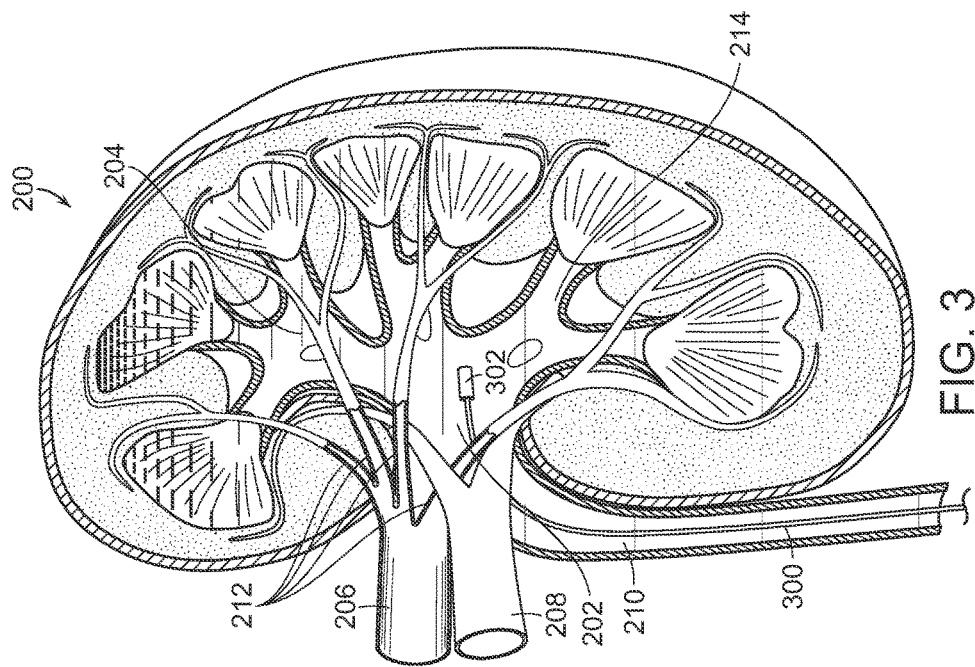
FIG. 2 is a cross-sectional view illustrating a kidney and a medium within the renal pelvic anatomy of the kidney in accordance with an embodiment of the present technology.

In some embodiments, a medium, such as a fluid, a particulate, a solution, and/or a colloid, within the renal pelvic anatomy can be activated to cause neuromodulation of nearby renal nerves. For example, a naturally-occurring medium (e.g., urine) or an artificially-introduced medium (e.g., saline) within the renal pelvic anatomy can be heated, cooled, energized, or otherwise activated in a manner sufficient to cause neuromodulation of renal nerves (e.g., afferent renal nerves or a combination of afferent and efferent renal nerves) around the renal pelvic anatomy. FIG. 2 is a cross-sectional view illustrating a kidney 200 including a renal pelvis 202 and a medium 204 within the renal pelvis 202. As shown in FIG. 2, the kidney 200 can further include a renal artery 206, a renal vein 208, and a ureter 210 extending from the renal pelvis 202. The renal artery 206 can branch into a plurality of renal branch arteries 212 of the kidney 200. The renal pelvis 202 can branch into a plurality of calyces 214 (one labeled) of the kidney 200. The medium 204 can enhance the distribution of a neuromodulating effect across the relatively large and irregular surface of the renal pelvic anatomy. The medium 204 can be introduced, for example, through the ureter 210, e.g., via a needle (not shown) or a catheter (not shown). In some embodiments, the ureter 210 can be at least partially blocked (e.g., clamped) to at least partially maintain the renal pelvic anatomy in a full state. The relatively-shallow positioning of the afferent renal nerves around the renal pelvis 202 can facilitate selective neuromodulation of the afferent rental nerves relative to the efferent renal nerves. For example, the medium 204 can be activated in a manner that causes therapeutically-effective renal neuromodulation in a zone within about 3 mm (e.g., within about 2 mm or within about 1.5 mm) of an inner surface of the renal pelvic wall. In some cases, the epithelium of the renal pelvic anatomy can recover from such a treatment, and all or most of the modulated nerves can remain non-functional.

One or more of the treatment modalities discussed above can be used to activate the medium 204 from an external device outside of the body. For example, the medium 204 can be heated using ultrasound (e.g., HIFU) directed into the renal pelvis 202 from an external ultrasound transducer device (not shown) located outside the body. When the ultrasound is applied, the location/orientation of the renal pelvis 202 relative to the external ultrasound transducer device and/or the relatively large size of the renal pelvis 202 may reduce the need for exact placement of a focal zone. In some embodiments, for example, the medium 204 can absorb and distribute heat relatively evenly over the renal pelvic wall even if the focal zone is not centrally positioned in the renal pelvis 202. Furthermore, because the renal pelvis 202 is relatively large, the likelihood of locating the focal zone at an undesirable location may be relatively low. In some embodiments, the medium 204 can be artificially introduced and selected to enhance neuromodulation. For example, the medium 204 can include a microbubble contrast agent or another material configured to increase the heating effect of ultrasound. Suitable microbubble contrast agents can have shells (e.g., made from albumin, lipid, or galactose) and gas cores (e.g., including air). In other embodiments, focused ultrasound can be used to neuromodulate portions of the renal pelvic anatomy without the medium 204.

Figure 3:
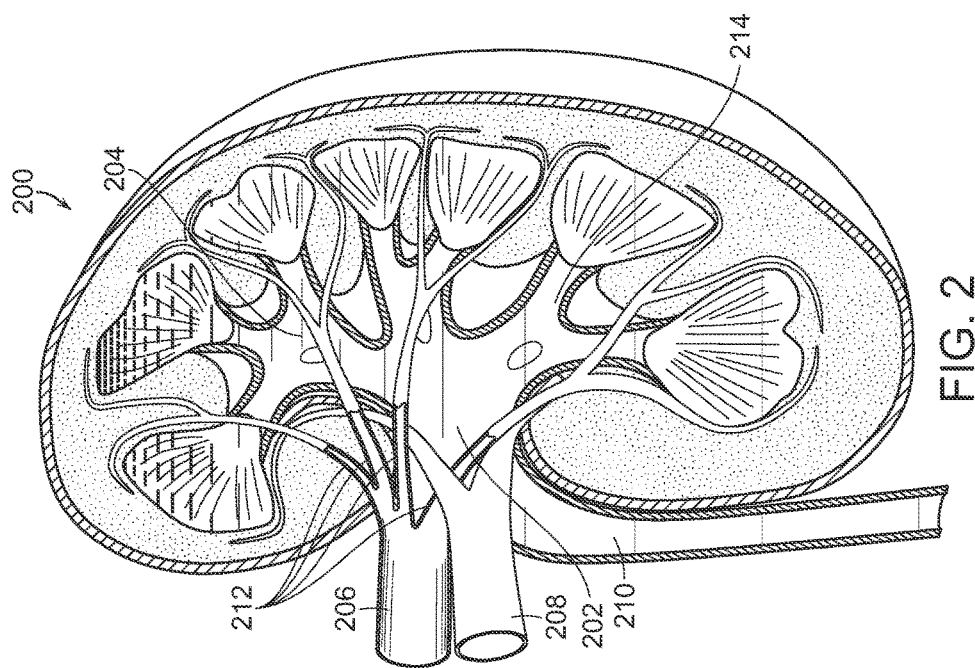
FIG. 3 is a cross-sectional view of the kidney and medium of FIG. 2 and a treatment device including a therapeutic element within the renal pelvic anatomy in accordance with an embodiment of the present technology.

In other embodiments, the medium 204 can be activated using an electrode or another therapeutic element located within the renal pelvis 202. FIG. 3 is a cross-sectional view illustrating a treatment device including a shaft 300 extending through the ureter 210 and a therapeutic element 302 at a distal portion of the shaft 300 within the renal pelvis 202. In some embodiments, the shaft 300 and the therapeutic element 302 can be portions of a treatment device at least partially corresponding to the first treatment device 102 shown in FIG. 1. With reference to FIG. 3, the therapeutic element 302 can be configured to activate the medium 204. For example, the therapeutic element 302 can include an electrode (not shown) (e.g., a radiofrequency electrode or a microwave electrode), a cryotherapeutic cooling assembly (not shown), a direct heating element (not shown), or another suitable activating component. In some embodiments, the therapeutic element 302 can include an opening (not shown) and can be configured to chemically activate the medium 204 by introducing a chemical into the medium 204 via the opening. In these and other embodiments, the therapeutic element 302 can further include an electrode (not shown) configured to deliver at least a portion of the chemical into the renal pelvic wall by electrophoresis.

Figure 4:
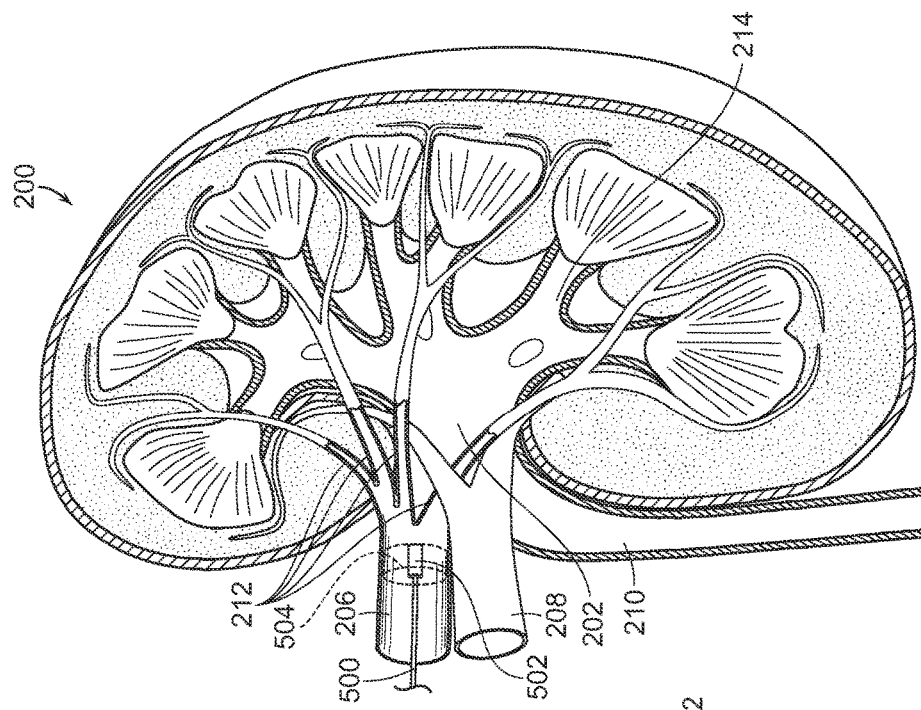
FIG. 4 is a cross-sectional view of the kidney, medium, and treatment device of FIG. 3 illustrating moving the therapeutic element to treatment locations within the renal pelvic anatomy in accordance with an embodiment of the present technology.

In some embodiments, therapeutic neuromodulation can be via the therapeutic element 302 and not via the medium 204. FIG. 4, for example, is a cross-sectional view illustrating moving the therapeutic element 302 between a first treatment location 400 and a second treatment location 402 during a treatment procedure. The shaft 300, for example, can be steerable (e.g., via one or more pull wires, a steerable guide or sheath catheter, etc.) and can be configured to sequentially move the therapeutic element 302 into the first and second treatment locations 400, 402. At the first treatment location 400, the therapeutic element 302 can contact or be in close proximity to a portion of the renal pelvic wall near the renal artery 206. At the second treatment location 402, the therapeutic element 302 can contact or be in close proximity to a wall of one of the calyces 214. A variety of other suitable treatment locations are also possible throughout the renal pelvic anatomy. Furthermore, a treatment procedure can include treatment at any suitable number of treatment locations, e.g., a single treatment location, two treatment locations (as shown in FIG. 4), or more than two treatment locations. The treatment locations can correspond to portions of the renal pelvic anatomy proximate relatively-high concentrations of afferent renal nerves. At each treatment location, the therapeutic element 302 can be activated to cause modulation of nerves proximate the treatment location. Activating the therapeutic element 302 can include, for example, heating, cooling, electrifying, or applying another suitable treatment modality at the treatment location. Activating the therapeutic element 302 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the therapeutic element 302 can be configured to introduce (e.g., inject) a chemical (e.g., a drug) into tissue at the treatment location. Such chemicals or agents can be applied at various concentrations depending on treatment location and the relative depth of the target nerves.

The therapeutic element 302 can be configured to accommodate the anatomy of the renal pelvis 202 and/or another suitable structure. For example, the therapeutic element 302 can include a balloon (not shown) configured to inflate to a shape generally corresponding to the shape of the renal pelvis 202. The balloon can be configured to deliver cryotherapeutic cooling or another suitable treatment modality over all or a portion the renal pelvis 202. In these and other embodiments, the therapeutic element 302 can be configured to apply a suitable treatment modality at a relatively shallow depth to avoid disrupting structures beyond the targeted renal nerves. For example, the therapeutic element 302 can include a plurality of electrodes (not shown) having a bipolar configuration, which can facilitate shallower treatment than other configurations. In another example, the therapeutic element 302 can include a plurality of heating elements (not shown) for directly applying heat at the treatment location. In some embodiments, this arrangement is expected to form shallower lesions in the wall of the renal pelvis 202 or a wall of one of the calyces 214 as compared with certain other energy modalities. Moreover, in some embodiments, therapy using direct heat application may require less power to operate than several other energy modalities. During a treatment procedure in which the therapeutic element 302 is configured to cause neuromodulation directly, the medium 204 can shape the renal pelvis 202 (e.g., in an open and/or slightly-distended state) to facilitate accurate placement of the therapeutic element 302. In other embodiments, the therapeutic element 302 can be used to neuromodulate portions of the renal pelvis 202 without the medium 204.

The medium 204 can have other functions in addition to or instead of being a vehicle for neuromodulation and shaping the renal pelvis 202. For example, since afferent renal nerves can carry a visceral pain signal, it can be useful to accompany neuromodulation of afferent renal nerves with local anesthesia. In some embodiments, a local anesthetic agent (e.g., procaine) can be introduced into the renal pelvis 202, e.g., via an opening (not shown) in the therapeutic element 302. Since nerve endings around the renal pelvis 202 are relatively shallow, the anesthetic agent can be highly localized and still effective. Furthermore, in some embodiments the medium 204 can be configured to facilitate imaging (e.g., magnetic resonance, computed tomography, fluoroscopy, ultrasound (e.g., intravascular or intraluminal), optical coherence tomography, or another suitable imaging modality) during a treatment procedure. For example, the medium 204 can include a contrast material, e.g., a contrast material configured to preferentially absorb light at wavelengths between about 500 nm and about 1100 nm. Suitable contrast materials include, for example, indocyanine green, methylene blue, toluidine blue, aminolevulinic acid, chlorin compounds, phthalocyanines, porphyrins, purpurins, and texaphyrins, among others. Imaging the renal pelvic anatomy can be used to identify portions of the renal pelvic anatomy suitable for treatment and/or to guide execution of a treatment within the renal pelvic anatomy. Guiding execution can include, for example, guiding placement of the therapeutic element 302 (e.g., by guiding steering operations of the shaft 300) and/or guiding placement of a focal zone of a focused ultrasound device.

In some embodiments, the medium 204 can help to protect the inner epithelium of the renal pelvic anatomy. For example, the medium 204 can include an epithelial-protective agent (e.g., polyethylene glycol) configured to preserve tissue integrity or otherwise reduce damage to epithelial cells while nerves proximate the epithelial cells are modulated. Similarly, the medium 204 can be cooled to counteract heat used to modulate the nerves proximate the epithelial cells. For example, the therapeutic element 302 can be configured to cool the medium 204. When the medium 204 protects the epithelial cells (e.g., via an epithelial-protective agent and/or cooling), the proximate nerves can be modulated, for example, with focused ultrasound. The focal zone of the focused ultrasound can include a maximum-intensity portion closer to the nerves being modulated than to the epithelial cells being protected. Placement of the focal zone and the protective effect of the medium 204 can function cooperatively to cause a relatively-steep temperature gradient between the epithelial cells and the nerves.

Other treatment procedures for selective modulation of afferent renal nerves in accordance with embodiments of the present technology are also possible. Treatment procedures for selective modulation of afferent renal nerves in accordance with embodiments of the present technology are expected to improve one or more measurable physiological parameters in patients corresponding to systemic sympathetic overactivity or hyperactivity. For example, the treatment procedures are expected to reduce MSNA (e.g., at least about 10%) and/or whole body norepinephrine spillover (e.g., at least about 20%) in patients. These and other clinical effects are expected to be detectable immediately after a treatment procedure or after a delay, e.g., of 1, 2, or 3 months.

VI. Selected Examples Of Treatment Procedures For Selective Modulation Of Efferent Renal Nerves Treatment procedures for selective modulation of efferent renal nerves in accordance with embodiments of the present technology can include applying a treatment modality at one or more treatment locations proximate a structure having a relatively-high concentration of efferent renal nerves and/or closer to efferent renal nerves than afferent renal nerves. In some embodiments, the treatment locations can be proximate portions of the renal artery 206 and/or the renal branch arteries 212 near the renal parenchyma. Portions of the renal plexus (not shown) proximate the treatment locations can have lower concentrations of afferent renal nerves than other portions of renal plexus. For example, the portions of the renal plexus proximate the treatment locations can have less than about 50% (e.g., less than about 25%) of a concentration of afferent renal nerves at a portion of the renal plexus proximate an ostium (not shown) of the renal artery 206. A therapeutic element of a treatment device can be positioned at a treatment location within the renal artery, for example, via a catheterization path including the femoral artery and the aorta or another suitable catheterization path, e.g., a radial or brachial catheterization path. Catheterization can be guided, for example, using imaging, e.g., magnetic resonance, computed tomography, fluoroscopy, ultrasound (e.g., intravascular or intraluminal), optical coherence tomography, or another suitable imaging modality.

Figure 5:
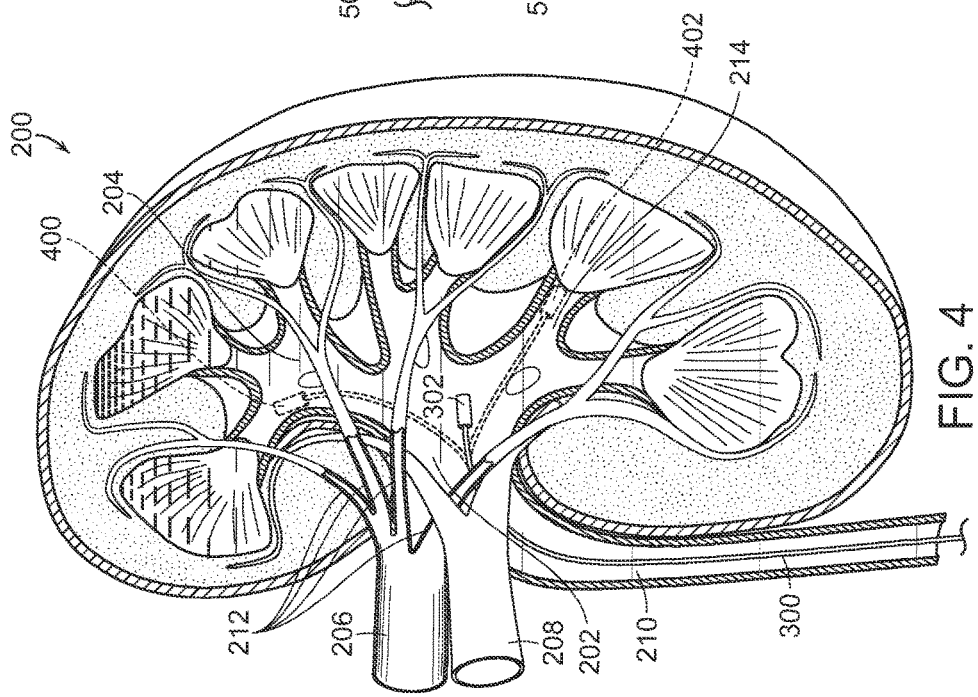
FIG. 5 is a cross-sectional view illustrating a kidney and a treatment device including a therapeutic element within the renal artery of the kidney in accordance with an embodiment of the present technology.
Figure 6:
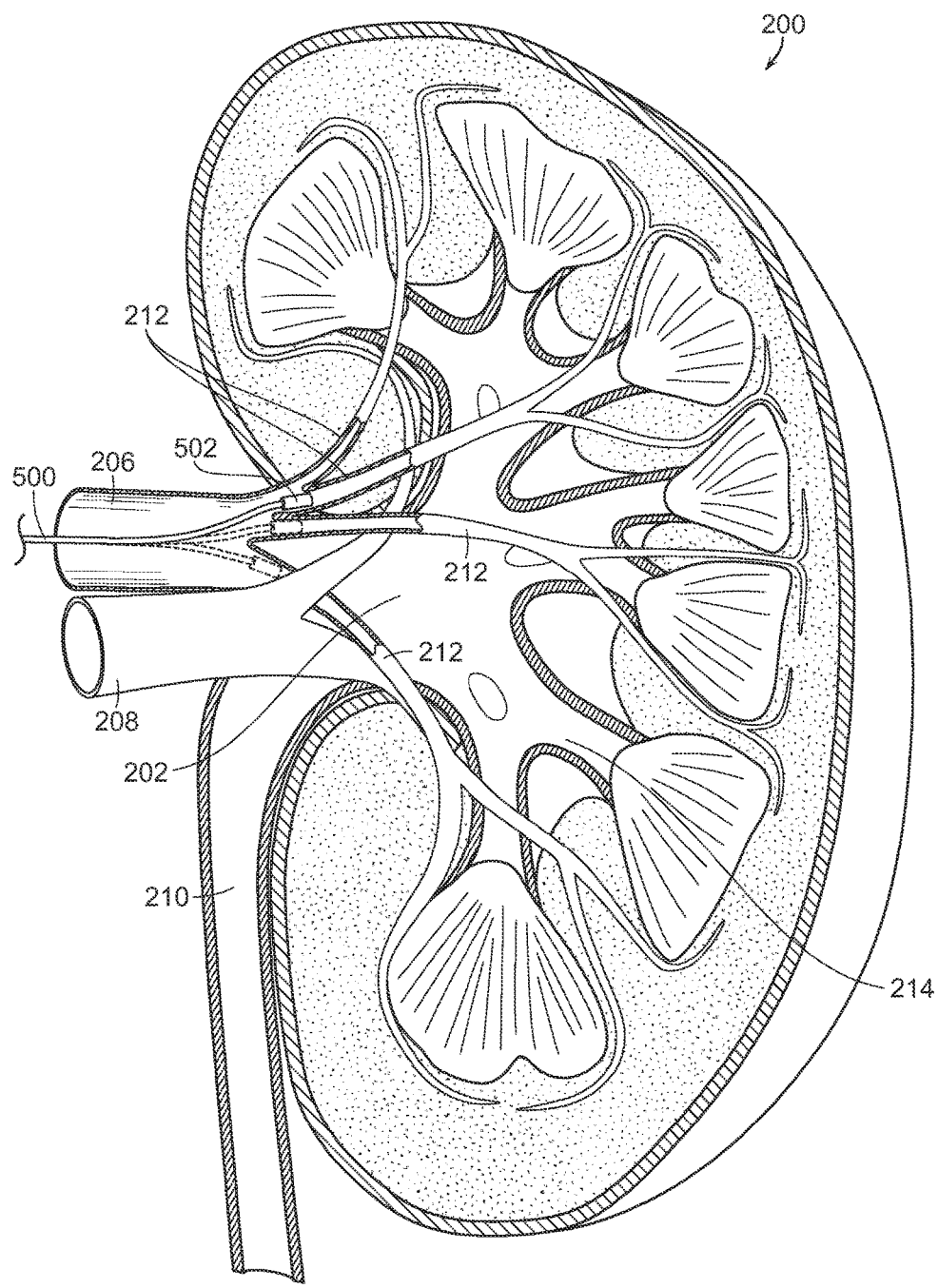
FIG. 6 is a cross-sectional view of the kidney and treatment device of FIG. 5 illustrating moving the therapeutic element to treatment locations within the renal branch arteries of the kidney in accordance with an embodiment of the present technology.

FIG. 5 is a cross-sectional view showing neuromodulation at a treatment location within the renal artery 206. FIG. 6 is a cross-sectional view showing neuromodulation at treatment locations within the renal branch arteries 212. Referring to FIGS. 5 and 6 together, a treatment device including a shaft 500 and a therapeutic element 502 can be extended toward the renal artery 206 to locate the therapeutic element 502 at a treatment location within the renal artery 206 and/or the renal branch arteries 212. The therapeutic element 502 can be configured for neuromodulation at the treatment location via a suitable treatment modality, e.g., cryotherapeutic, direct heat, electrode-based, transducer-based, or chemical-based. In some embodiments, the shaft 500 and the therapeutic element 502 can be portions of a treatment device at least partially corresponding to the first treatment device 102 shown in FIG. 1. The shaft 500 can be steerable (e.g., via one or more pull wires, a steerable guide or sheath catheter, etc.) and can be configured to move the therapeutic element 502 between treatment locations. At each treatment location, the therapeutic element 502 can be activated to cause modulation of nerves proximate the treatment location. Activating the therapeutic element 502 can include, for example, heating, cooling, stimulating, or applying another suitable treatment modality at the treatment location. Activating the therapeutic element 502 can further include applying various energy modalities at varying power levels, intensities and for various durations for achieving modulation of nerves proximate the treatment location. In some embodiments, power levels, intensities and treatment duration can be determined and employed using various algorithms for ensuring modulation of nerves at select distances (e.g., depths) away from the treatment location. Additionally, in some embodiments, the therapeutic element 502 can be configured to introduce (e.g., inject) a chemical (e.g., a drug or other agent) into target tissue at the treatment location. Such chemicals or agents can be applied at various concentrations depending on treatment location and the relative depth of the target nerves.

In some embodiments, the therapeutic element 502 can be configured to radially expand into a deployed state 504 at the treatment location. In the deployed state 504, the therapeutic element 502 can be configured to contact an inner wall of the renal artery 206 and to form a fully-circumferential lesion without the need for repositioning. For example, the therapeutic element 502 can be configured to form a lesion or series of lesions (e.g., a helical/spiral lesion or a discontinuous lesion) that is fully-circumferential overall, but generally non-circumferential at longitudinal segments of the treatment location. This can facilitate precise and efficient treatment with a low possibility of vessel stenosis. In other embodiments, the therapeutic element 502 can be configured to form a partially-circumferential lesion or a fully-circumferential lesion at a single longitudinal segment of the treatment location. During treatment, the therapeutic element 502 can be configured to partially or fully occlude the renal artery 206. Partial occlusion can be useful, for example, to reduce renal ischemia, and full occlusion can be useful, for example, to reduce interference (e.g., warming or cooling) caused by blood flow through the treatment location. In some embodiments, the therapeutic element 502 can be configured to cause therapeutically-effective neuromodulation (e.g., using ultrasound energy) without contacting a vessel wall.

The therapeutic element 502 can be configured to accommodate the anatomy of the renal artery 206 and/or the renal branch arteries 212, and/or another suitable structure. For example, the therapeutic element 502 can include a balloon (not shown) configured to inflate to a size generally corresponding to the internal size of the renal artery 206 and/or the renal branch arteries 212, and/or another suitable structure. In some embodiments, the therapeutic element 502 can be an implantable device and a treatment procedure can include locating the therapeutic element 502 at the treatment location using the shaft 500 fixing the therapeutic element 502 at the treatment location, separating the therapeutic element 502 from the shaft 500, and withdrawing the shaft 500. Other treatment procedures for selective modulation of efferent renal nerves in accordance with embodiments of the present technology are also possible.

Treatment procedures for selective modulation of efferent renal nerves in accordance with embodiments of the present technology are expected to improve one or more measurable physiological parameters in patients corresponding to systemic sympathetic overactivity or hyperactivity. For example, the treatment procedures are expected to reduce MSNA (e.g., at least about 10%) and/or whole body norepinephrine spillover (e.g., at least about 20%) in patients. These and other clinical effects are expected to be detectable immediately after a treatment procedure or after a delay, e.g., of 1, 2, or 3 months.

VII. Methods For Selective Renal Neuromodulation

Disclosed herein are several embodiments of methods directed to selective neuromodulation of afferent and/or efferent renal nerves. The methods disclosed herein may represent various advantages over a number of conventional approaches and techniques in that they allow for the potential targeting of elevated sympathetic drive, which may be a key mediator of multiple manifestations of cardiovascular, metabolic and endocrine-related conditions. Also, the disclosed methods provide for localized treatment and limited duration treatment regimens (e.g., one-time treatment), thereby reducing patient long-term treatment compliance issues.

In certain embodiments, the methods provided herein comprise performing selective renal neuromodulation, thereby decreasing sympathetic renal nerve activity and decreasing central sympathetic drive. Selective renal neuromodulation may be repeated one or more times at various intervals until a desired sympathetic nerve activity level or another therapeutic benchmark is reached. In one embodiment, for example, a decrease in sympathetic nerve activity may be observed via a marker of sympathetic nerve activity in patients, such as decreased levels of plasma norepinephrine (noradrenaline). Other measures or markers of sympathetic nerve activity can include MSNA, norepinephrine spillover, and/or heart rate variability. In another embodiment, other measurable physiological parameters or markers, such as improved blood pressure control, improved blood glucose regulation, etc., can be used to assess efficacy of the thermal modulation treatment for patients.

In certain embodiments of the methods provided herein, selective renal neuromodulation is expected to result in a change in sympathetic nerve activity over a specific timeframe. For example, in certain of these embodiments, sympathetic nerve activity levels are decreased over an extended timeframe, e.g., within 1 month, 2 months, 3 months, 6 months, 9 months or 12 months post-neuromodulation.

In several embodiments, the methods disclosed herein may comprise an additional step of measuring sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure. In certain embodiments, a baseline sympathetic nerve activity level is derived from the subject undergoing treatment. For example, baseline sympathetic nerve activity level may be measured in the subject at one or more timepoints prior to treatment. A baseline sympathetic nerve activity value may represent sympathetic nerve activity at a specific timepoint before neuromodulation, or it may represent an average activity level at two or more timepoints prior to neuromodulation. In certain embodiments, the baseline value is based on sympathetic nerve activity immediately prior to treatment (e.g., after the subject has already been catheterized). Alternatively, a baseline value may be derived from a standard value for sympathetic nerve activity observed across the population as a whole or across a particular subpopulation. In certain embodiments, post-neuromodulation sympathetic nerve activity levels are measured in extended timeframes post-neuromodulation, e.g., 3 months, 6 months or 12 months post-neuromodulation.

In certain embodiments of the methods provided herein, the methods are designed to decrease sympathetic nerve activity to a target level. In these embodiments, the methods include a step of measuring sympathetic nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease sympathetic nerve activity below a baseline level without requiring a particular target activity level.

In addition to affecting the sympathetic nerve activity or central sympathetic drive in a patient, selective renal neuromodulation (e.g., selective afferent or selective efferent renal neuromodulation) may efficaciously treat other measurable physiological parameter(s) or sequela corresponding to overactivity or hyperactivity of central sympathetic drive. For example, in some embodiments, selective renal neuromodulation may address metabolic issues (e.g., obesity, metabolic syndrome, insulin resistance), cardiovascular risk (e.g., high cholesterol, hypertension, LVH) and endocrine issues (e.g., sequela associated with polycystic ovary syndrome, erectile dysfunction). These and other results can occur at various times, e.g., directly following selective renal neuromodulation or within about 1 month, 3 months, 6 months, a year, or a longer period following selective renal neuromodulation.

As discussed previously, the progression of many cardiovascular, metabolic and/or endocrine disease states may be related to sympathetic overactivity and, correspondingly, the degree of sympathoexcitation in a patient may be related to the severity of the clinical presentation of the respective conditions. The kidneys can be both a cause (directly via afferent nerve fibers and indirectly via efferent nerve fibers) and a target (via efferent sympathetic nerves) of elevated central sympathetic drive. In some embodiments, selective renal neuromodulation can be used to reduce central sympathetic drive in a patient in a manner that treats the patient for the disease state (e.g., cardiovascular, metabolic, endocrine, etc.). In some embodiments, for example, MSNA can be reduced by at least about 5%, about 10%, or about 20% in the patient within about three months after at least partially inhibiting sympathetic neural activity in afferent nerves proximate a renal pelvis, a ureteropelvic junction, a major calyx, a minor calyx, and/or other suitable structure. Similarly, in some instances whole body norepinephrine spillover to plasma can be reduced at least about 20% in the patient within about three months after at least partially inhibiting sympathetic neural activity in afferent nerves proximate a renal pelvis, a ureteropelvic junction, a major calyx, a minor calyx, and/or other suitable structure. In another embodiment, MSNA can be reduced by at least about 5%, about 10%, or about 20% in the patient within about three months after at least partially inhibiting sympathetic neural activity in efferent nerves proximate a renal artery and/or a renal branch artery, and/or another suitable structure. Similarly, whole body norepinephrine spillover to plasma can be reduced at least about 20% in the patient within about three months after at least partially inhibiting sympathetic neural activity in efferent nerves proximate a renal artery and/or a renal branch artery, and/or another suitable structure. Additionally, measured renal norepinephrine content (e.g., assessed via biopsy, assessed in real-time via intravascular blood collection techniques, etc.) can be reduced (e.g., at least about 5%, 10%, or by at least 20%) in the patient within about three months after at least partially inhibiting sympathetic neural activity in efferent nerves proximate a renal artery innervating the kidney.

In one prophetic example, a patient diagnosed or suspected as having sympathetic overactivity can be subjected to a baseline assessment indicating a first set of measurable parameters corresponding to sympathetic overactivity. Such parameters can include, for example, blood pressure, cholesterol levels, blood glucose levels, fasting blood insulin levels, measures of insulin sensitivity, and aldosterone levels. Following baseline assessment, the patient can be subjected to a selective renal neuromodulation procedure (e.g., selective afferent neuromodulation, selective efferent neuromodulation). Such a procedure can, for example, include any of the treatment modalities described herein or another treatment modality in accordance with the present technology. The treatment can be performed on afferent or efferent nerves innervating one or both kidneys of the patient. Following the treatment (e.g., 1, 3, 6, or 12 months following the treatment), the patient can be subjected to a follow-up assessment. The follow-up assessment can indicate a measurable improvement in one or more physiological parameters corresponding to the sympathetic overactivity.

The methods described herein address the sympathetic excess that is thought to be an underlying cause or a central mechanism through which diseased or damaged kidneys manifests their multiple deleterious effects on patients. In contrast, known therapies currently prescribed for this patient population typically address only specific manifestations of the various sequelae. Additionally, these known therapies can have significant limitations including limited efficacy, undesirable side effects and can be subject to adverse or undesirable drug interactions when used in combination. Additionally, conventional therapies require the patient to remain compliant with the treatment regimen over time. In contrast, selective renal neuromodulation can be a one-time treatment that would be expected to have durable benefits to inhibit long-term disease progression and thereby achieve a favorable patient outcome.

In some embodiments, patients diagnosed with sympathetic overactivity and/or diseased or damaged kidneys can be treated with selective renal neuromodulation alone. However, in other embodiments, these patients can be treated with combinations of therapies for treating both primary causative modes as well as sequelae of the cardiovascular, metabolic and/or endocrine related conditions. For example, combinations of therapies can be tailored based on specific manifestations of the disease in a particular patient. In a specific example, patients having elevated or overactive sympathetic drive and presenting hypertension can be treated with both anti-hypertensive therapy (e.g., drugs) and selective renal neuromodulation.

In another example, selective renal neuromodulation can be combined with cholesterol lowering agents (e.g., statins), hormonal therapy (e.g., estrogen-progestin contraceptive), and phosphodiesterase type 5 (PDE5) inhibitors (e.g., sildenafil, tadalafil, vardenafil, avanafil, etc.) as well as weight loss and lifestyle change recommendations/programs.

Treatment of conditions relating to or resulting from sympathetic overactivity may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Figure 7:
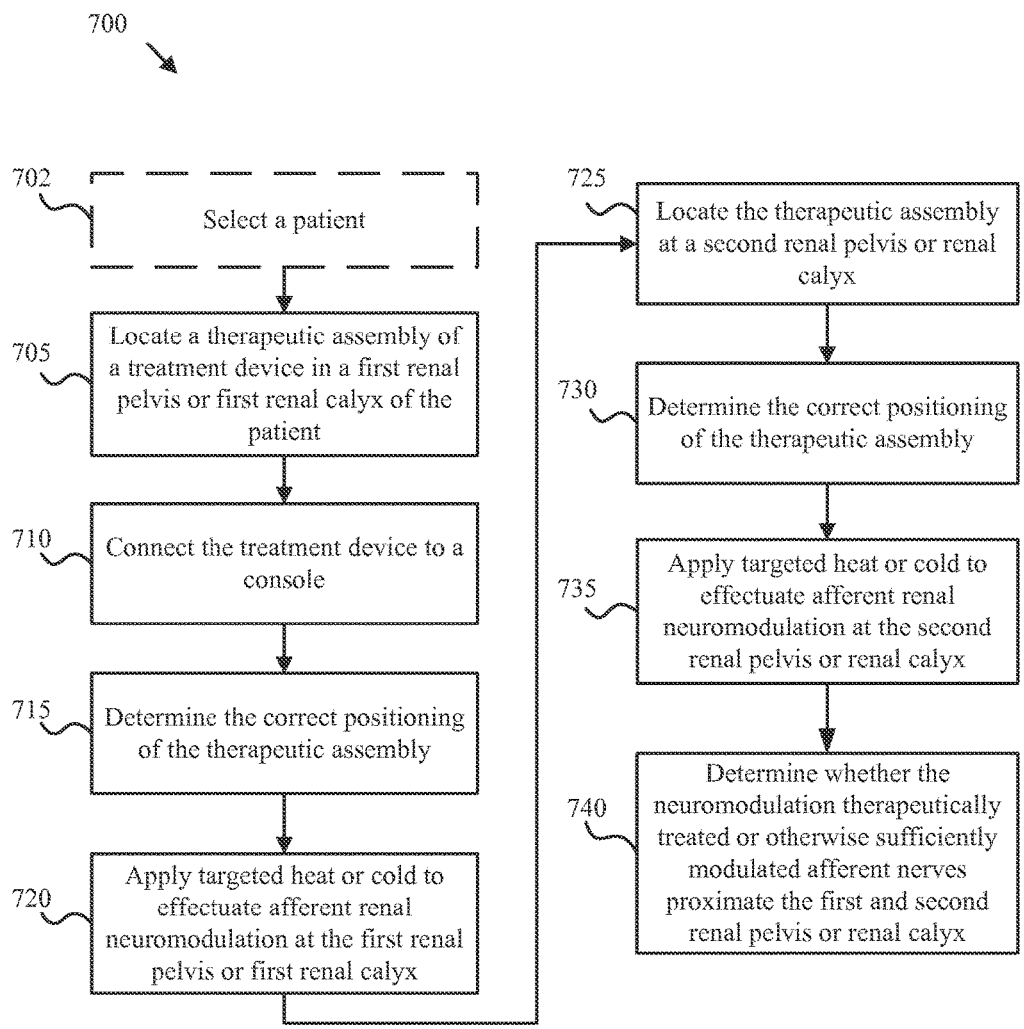
FIG. 7 is a block diagram illustrating a method of selectively modulating afferent renal nerves in accordance with an embodiment of the present technology.

FIG. 7 is a block diagram illustrating a method 700 of selectively modulating afferent renal nerves using the system 100 described above with reference to FIGS. 1-4. With reference to FIGS. 1-4 and 7 together, the method 700 can optionally include selecting a suitable candidate patient for performing selective afferent renal neuromodulation (block 702). The method 700 can include locating the therapeutic element 302 in a delivery state (e.g., low-profile configuration) at a first target site in or near a first renal pelvis, a ureteropelvic junction, a major calyx, or a minor calyx (e.g., first renal pelvis or first renal calyx) (block 705). The first treatment device 102 and/or portions thereof (e.g., the therapeutic element 302) can be inserted into a guide catheter or sheath to facilitate delivery of the therapeutic element 302 through a ureter connected to the renal pelvis. In certain embodiments, for example, the first treatment device 102 can be configured to fit within an 8 Fr guide catheter or smaller (e.g., 7 Fr, 6 Fr, etc.) to access the ureter, the renal pelvis anatomy and/or renal calyces. A guide wire (not shown), if present, can be used to manipulate and enhance control of the shaft 300 and the therapeutic element 302 (e.g., in an over-the-wire or a rapid-exchange configuration). In some embodiments, radiopaque markers and/or markings on the first treatment device 102 and/or the guide wire can facilitate placement of the therapeutic element 302 at the first target site (e.g., first renal pelvis or first renal calyx of a patient). In some embodiments, a contrast material can be delivered distally beyond the therapeutic element 302, and fluoroscopy and/or other suitable imaging techniques can be used to aid in placement of the therapeutic element 302 at the first target site.

The method 700 can further include connecting the first treatment device 102 to the console 106 (block 710), and determining whether the therapeutic element 302 is in the correct position at the target site and/or whether the therapeutic element (e.g., electrodes, transducers or cryotherapy balloon) is functioning properly (block 715). Once the therapeutic element 302 is properly located at the first target site and no malfunctions are detected, the console 106 can be manipulated to initiate application of an energy field to the target site to cause electrically-induced and/or thermally-induced neuromodulation of afferent nerve fibers innervating the kidney (e.g., using electrodes, transducers, or cryotherapeutic devices). Accordingly, heating and/or cooling of the therapeutic element 302 causes modulation of afferent renal nerves at the first target site (block 720).

The therapeutic element 302 can then be located at a second target site in or near a second renal pelvis, a ureteropelvic junction, a major calyx, or a minor calyx (e.g., second renal pelvis or second renal calyx) (block 725), and correct positioning of the therapeutic element 302 can be determined (block 730). In selected embodiments, a contrast material can be delivered distally beyond the therapeutic element 302 and fluoroscopy and/or other suitable imaging techniques can be used to locate the second renal pelvis or second renal calyx. The method 700 continues by applying targeted heat or cold to effectuate afferent renal neuromodulation at the second target site (block 735).

After providing the therapeutically-effective neuromodulation energy (e.g., cryogenic cooling, RF energy, ultrasound energy, etc.), the method 700 may also include determining whether the neuromodulation therapeutically treated the patient for one or more conditions associated with sympathetic overactivity or otherwise sufficiently modulated afferent nerves or other neural structures proximate the first and second target sites (block 740). For example, the process of determining whether the neuromodulation therapeutically treated the nerves can include determining whether nerves were sufficiently modulated or otherwise disrupted to reduce, suppress, inhibit, block or otherwise affect the afferent (and/or efferent) renal signals (e.g., by evaluation of suitable biomarkers, stimulation and recording of nerve signals, etc.). In a further embodiment, patient assessment could be performed at time intervals (e.g., 1 month, 3 months, 6 months, 12 months) following neuromodulation treatment. For example, the patient can be assessed for measurements of perceived pain, blood pressure control, blood glucose levels, and measures of sympathetic activity (e.g., MSNA, and/or renal norepinephrine spillover to plasma, whole body norepinephrine spillover, and heart rate variability).

Figure 8:
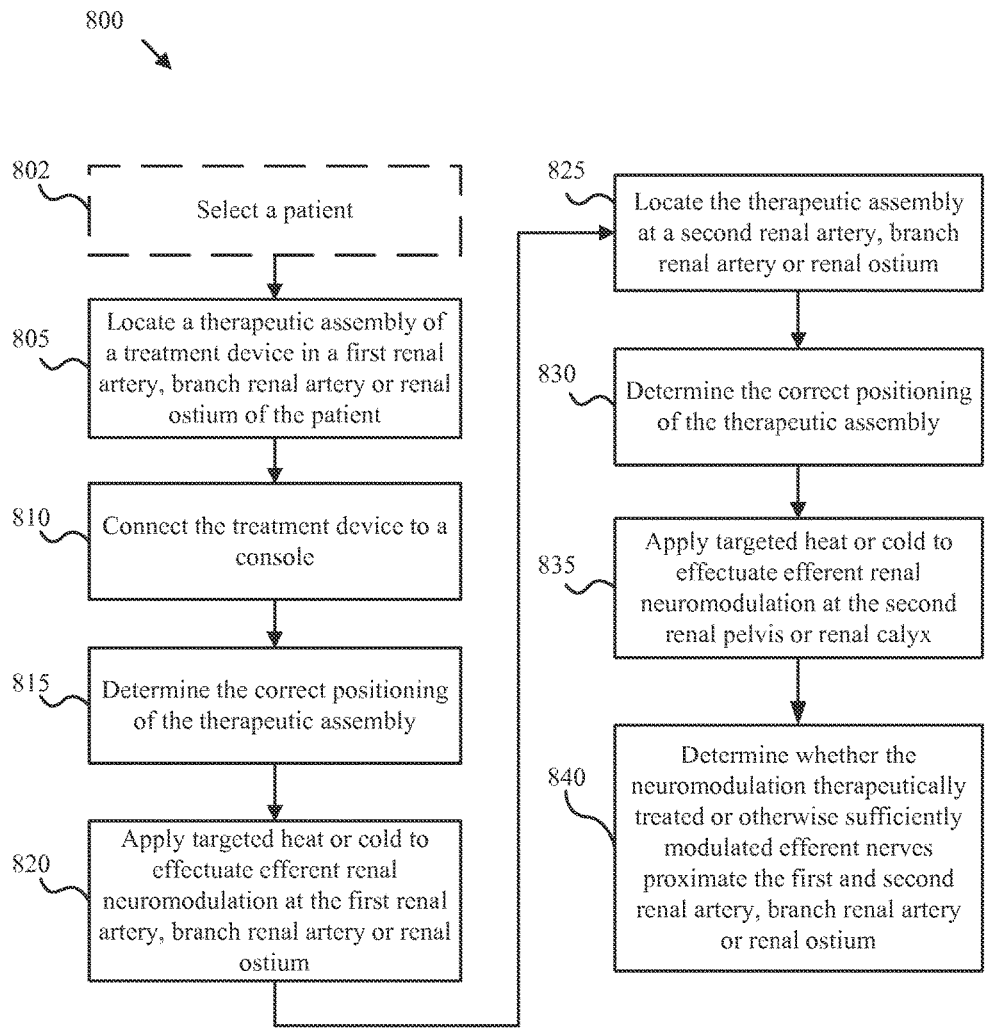
FIG. 8 is a block diagram illustrating a method of selectively modulating efferent renal nerves in accordance with an embodiment of the present technology.

FIG. 8 is another block diagram illustrating a method 800 of selectively modulating efferent renal nerves using the system 100 described above with reference to FIGS. 1 and 2 and FIGS. 5 and 6. With reference to FIGS. 1 and 2 and FIGS. 5-8 together, the method 800 can optionally include selecting a suitable candidate patient for performing selective efferent renal neuromodulation (block 802). In one embodiment, the patient has systemic sympathetic overactivity or hyperactivity and is diagnosed with cystinuria. In another embodiment, the patient has systemic sympathetic overactivity or hyperactivity and has been diagnosed as having an increased risk of developing kidney stones relative to the general population. The method 800 can include intravascularly locating the therapeutic element 502 in a delivery state (e.g., low-profile configuration) at a first target site in or near a first renal blood vessel (e.g., a first renal artery, a first renal branch artery) or a first renal ostium (block 805). The first treatment device 102 and/or portions thereof (e.g., the therapeutic element 502) can be inserted into a guide catheter or sheath to facilitate intravascular delivery of the therapeutic element 502. In certain embodiments, for example, the first treatment device 102 can be configured to fit within an 8 Fr guide catheter or smaller (e.g., 7 Fr, 6 Fr, etc.) to access the ureter, the renal pelvis anatomy and/or renal calyces). A guide wire (not shown), if present, can be used to manipulate and enhance control of the shaft 500 and the therapeutic element 502 (e.g., in an over-the-wire or a rapid-exchange configuration). Radiopaque markers and/or markings on the first treatment device 102 and/or the guide wire can, in some embodiments, facilitate placement of the therapeutic element 502 at the first target site (e.g., first renal artery or branch artery or a first renal ostium of a patient). In some embodiments, a contrast material can be delivered distally beyond the therapeutic element 502, and fluoroscopy and/or other suitable imaging techniques can be used to aid in placement of the therapeutic element 502 at the first target site.

The method 800 can further include connecting the first treatment device 102 to the console 106 (block 810). Further steps can include determining whether the therapeutic element 502 is in the correct position at the first target site and/or whether the therapeutic element 502 (e.g., electrodes, transducers or cryotherapy balloon) is properly functioning (block 815). Once the therapeutic element 502 is located at the first target site and no malfunctions are detected, the console 106 can be manipulated to initiate application of an energy field (e.g., using a suitable algorithm) to the first target site to cause electrically-induced and/or thermally-induced neuromodulation of efferent nerve fibers innervating the kidney (e.g., using electrodes, transducers or cryo-therapeutic devices). Accordingly, heating and/or cooling of the therapeutic element 502 causes modulation of efferent renal nerves at the first target site (block 820).

If desirable, the therapeutic element 502 can be located at a second target site in or near a second renal blood vessel (e.g., second renal artery, second renal branch artery or second renal ostium) (block 825), and correct positioning of the therapeutic element 502 can be determined (block 830). In selected embodiments, a contrast material can be delivered distally beyond the therapeutic element 502 and fluoroscopy and/or other suitable imaging techniques can be used to locate the second renal artery, second renal branch artery or second renal ostium. The method 800 continues by applying targeted thermal energy to effectuate efferent renal neuromodulation at the second target site (block 835).

After providing the therapeutically-effective neuromodulation energy (e.g., cryogenic cooling, RF energy, ultrasound energy, etc.), the method 800 may also include determining whether the neuromodulation therapeutically treated the patient for one or more conditions associated with sympathetic overactivity or otherwise sufficiently modulated efferent nerves or other neural structures proximate the first and/or second target sites (block 840). For example, the process of determining whether the neuromodulation therapeutically treated the efferent nerves can include determining whether nerves were sufficiently modulated or otherwise disrupted to reduce, suppress, inhibit, block or otherwise affect the efferent (and/or afferent) renal signals (e.g., by evaluation of suitable biomarkers, stimulation and recording of nerve signals, etc.). In a further embodiment, patient assessment could be performed at time intervals (e.g., 1 month, 3 months, 6 months, 12 months) following neuromodulation treatment. For example, the patient can be assessed for measurements of perceived pain, blood pressure control, blood glucose levels, and measures of sympathetic activity (e.g., MSNA, and/or renal norepinephrine spillover to plasma, whole body norepinephrine spillover, and heart rate variability).

Referring to FIGS. 7 and 8 together and in one example, the first treatment device 102 can be an RF energy emitting device and RF energy can be delivered through energy delivery elements or electrodes to one or more locations along the inner wall of the first target site for predetermined periods of time (e.g., 120 seconds). In some embodiments, multiple treatments (e.g., 4-6) may be administered in both the first and second target sites (e.g., in the left and right renal pelvis or renal arteries to achieve a desired coverage). An objective of a treatment may be, for example, to heat tissue to a desired depth (e.g., at least about 1.5 mm, at least about 2 mm, at least about 3 mm) to a temperature (e.g., about 65° C.) that would modulate one or more nerve fibers associated with or adjacent to one or more lesions formed in the vessel wall. A clinical objective of the procedure typically is to neuromodulate a sufficient number of renal nerves (e.g., selectively efferent or afferent nerves) to cause a reduction in central sympathetic drive and/or reduction in sympathetic tone or drive to the kidneys without, for example, disrupting renal function and while minimizing vessel trauma. If the objective of a treatment is met (e.g., tissue is heated to about 65° C. to a depth of about 1 mm to about 3 mm) the probability of modulating renal nerve tissue (e.g., altering nerve function) is high. In some embodiments, a single neuromodulation treatment procedure can provide for sufficient modulation of target sympathetic nerves (e.g., modulation of a sufficient number of nerve fibers) to provide a desired clinical outcome. In other embodiments, more than one treatment may be beneficial for modulating a desired number or volume of target sympathetic nerve fibers, and thereby achieve clinical success. In other embodiments, an objective may include reducing or eliminating target sympathetic nerve function completely.

In a specific example of using RF energy for renal nerve modulation, a clinician can commence treatment which causes the control algorithm 132 (FIG. 1) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time, i.e., in a linear manner. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment, $P_{MAX}$ is 10 watts, or in a further embodiment, $P_{MAX}$ is 6.5 watts. In some embodiments, $P_{MAX}$ can be about 6 watts to about 10 watts. Optionally, the power may be maintained at the maximum power $P_{MAX}$ for a desired period of time or up to the desired total treatment time (e.g., up to about 120 seconds) or until a specified temperature is reached or maintained for a specified time period.

In another specific example, the first treatment device 102 can be a cryogenic device and cryogenic cooling can be applied for one or more cycles (e.g., for 30 second increments, 60 second increments, 90 second increments, etc.) in one or more locations along the circumference and/or length of the first target site. The cooling cycles can be, for example, fixed periods or can be fully or partially dependent on detected temperatures (e.g., temperatures detected by a thermocouple (not shown) of the therapeutic element 302 or 502). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

In other embodiments, various steps in the methods 700 or 800 can be modified, omitted, and/or additional steps may be added. In further embodiments, the methods 700 or 800 can have a delay between applying therapeutically-effective neuromodulation energy at a first target site and applying therapeutically-effective neuromodulation energy at a second target site. For example, neuromodulation of the first target site can take place at a first treatment session, and neuromodulation of the second target site can take place at a second treatment session at a later time. In other embodiments, various steps of the methods 700 and 800 could be combined. In a specific example, therapeutically-effective neuromodulation energy can be delivered at a first target site in a renal artery (e.g., energy delivered intravascularly by catheter), and therapeutically-effective neuromodulation energy can be delivered (e.g., either prior to, concurrently with, or following energy delivery to the first target site) at a second target site in a renal pelvis (e.g., energy delivered via a catheterization path through the ureter and/or delivered extracorporeally). Accordingly, embodiments of the methods disclosed herein include neuromodulation of nerves proximate to renal blood vessel(s) and/or the renal pelvis. Without being bound by theory, in some embodiments it is believed that modulation of nerves proximate both the renal artery and the renal pelvis may provide for modulation of a higher percentage of afferent nerve fibers with respect to a total number of modulated nerve fibers.

As discussed previously, treatment procedures for selective modulation of afferent or efferent renal nerves in accordance with embodiments of the present technology are expected to improve at least one condition associated with renal sympathetic activity (e.g., overactivity or hyperactivity) and/or central sympathetic activity (e.g., overactivity or hyperactivity). For example, with respect to central sympathetic activity (e.g., overactivity or hyperactivity), modulation of renal nerves is expected to reduce muscle sympathetic nerve activity and/or whole body norepinephrine spillover in patients. These and other clinical effects are expected to be detectable immediately after a treatment procedure or after a delay, e.g., of 1, 2, or 3 months. In some instances, it may be useful to repeat selective renal neuromodulation, such as selective efferent or afferent renal neuromodulation, at the same treatment location or a different treatment location after a suitable delay, e.g., 1, 2, or 3 years. In still other embodiments, however, other suitable treatment regimens or techniques may be used.

VIII. Pertinent anatomy and physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal neuromodulation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The SNS is a branch of the autonomic nervous system along with the enteric nervous system and parasympathetic nervous system. It is always active at a basal level (called sympathetic tone) and becomes more active during times of stress. Like other parts of the nervous system, the SNS operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The SNS is responsible for up- and down-regulation of many homeostatic mechanisms in living organisms. Fibers from the SNS innervate tissues in almost every organ system, providing at least some regulatory function to physiological features as diverse as pupil diameter, gut motility, and urinary output. This response is also known as the sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the SNS and indirectly via catecholamines secreted from the adrenal medulla.

Science typically looks at the SNS as an automatic regulation system, that is, one that operates without the intervention of conscious thought. Some evolutionary theorists suggest that the SNS operated in early organisms to maintain survival as the SNS is responsible for priming the body for action. One example of this priming is in the moments before waking, in which sympathetic outflow spontaneously increases in preparation for action.

1. The Sympathetic Chain

Figure 9:
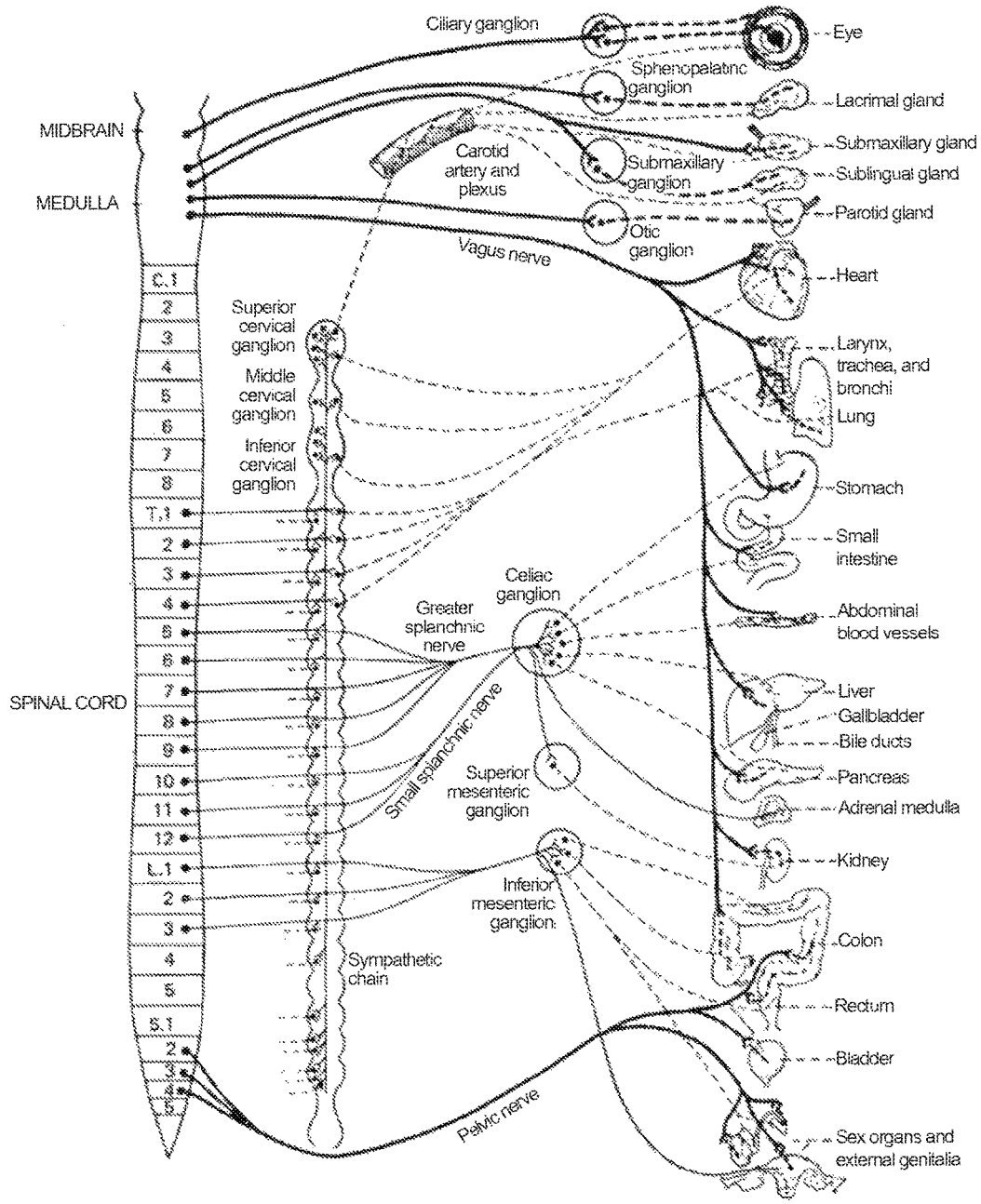
FIG. 9 is a conceptual diagram illustrating the sympathetic nervous system and how the brain communicates with the body via the sympathetic nervous system.

As shown in FIG. 9, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors that connect to either the paravertebral (which lie near the vertebral column) or prevertebral (which lie near the aortic bifurcation) ganglia extending alongside the spinal column.

In order to reach the target organs and glands, the axons travel long distances in the body. Many axons relay their message to a second cell through synaptic transmission. The first cell (the presynaptic cell) sends a neurotransmitter across the synaptic cleft (the space between the axon terminal of the first cell and the dendrite of the second cell) where it activates the second cell (the postsynaptic cell). The message is then propagated to the final destination.

In the SNS and other neuronal networks of the peripheral nervous system, these synapses are located at sites called ganglia, discussed above. The cell that sends its fiber to a ganglion is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands. The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Nerves of the Kidneys

Figure 10:
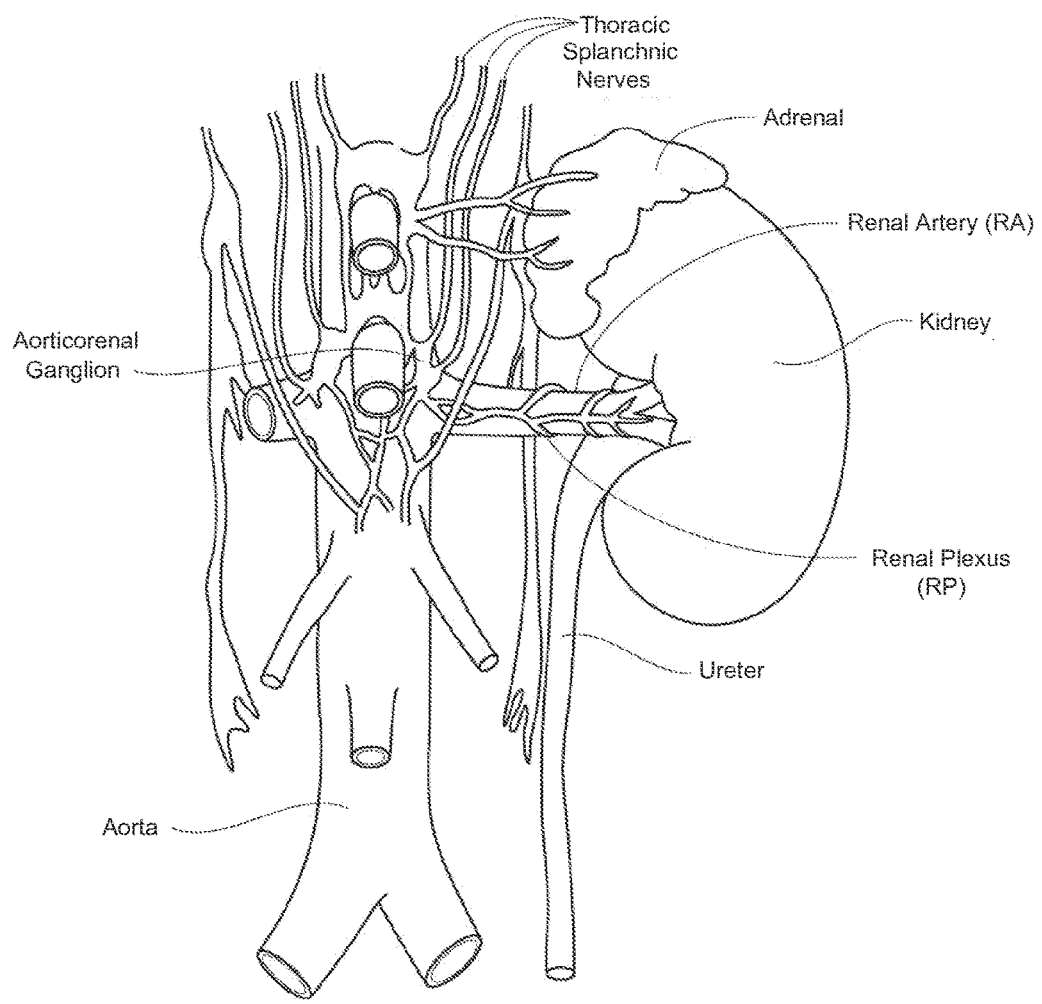
FIG. 10 is an enlarged anatomical view illustrating nerves innervating a left kidney to form a renal plexus surrounding a left renal artery.

As FIG. 10 shows, the kidney is innervated by the renal plexus RP, which is intimately associated with the renal artery RA. The renal plexus RP is an autonomic plexus that surrounds the renal artery RA and is embedded within the adventitia of the renal artery RA. The renal plexus RP extends along the renal artery RA until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate, widen bronchial passages, decrease motility (movement) of the large intestine, constrict blood vessels, increase peristalsis in the esophagus, cause pupil dilation, piloerection (goose bumps) and perspiration (sweating), and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing overactivity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine (NE) from the kidneys to plasma revealed increased renal NE spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced SNS overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 11A:
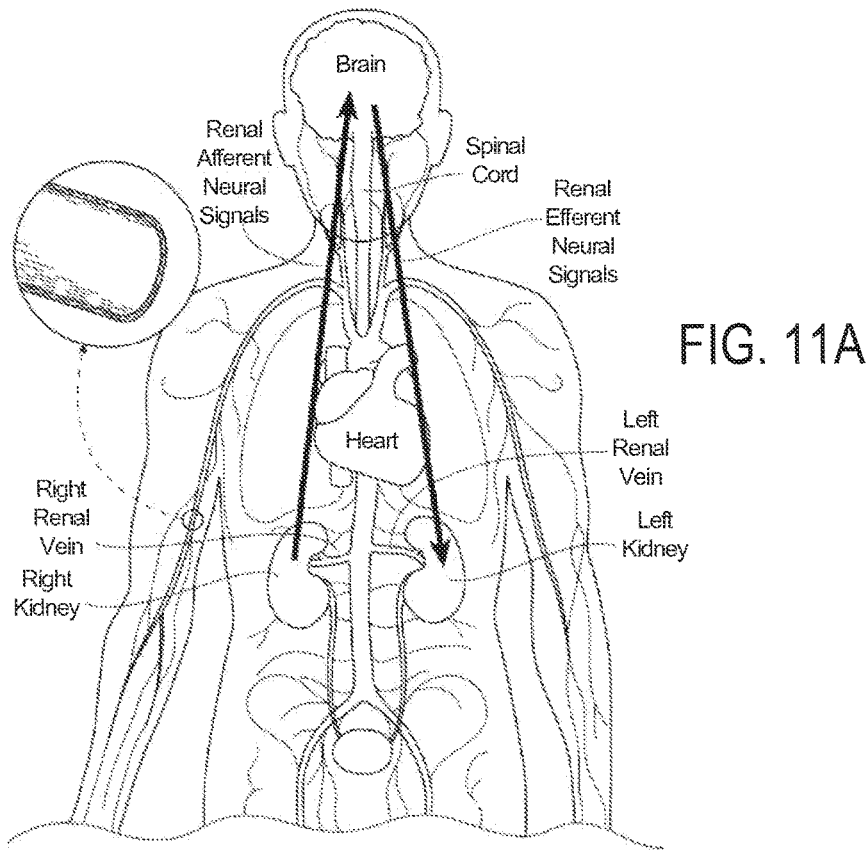
FIGS. 11A and 11B are anatomical and conceptual views, respectively, illustrating a human body including a brain and kidneys and neural efferent and afferent communication between the brain and kidneys.
Figure 11B:
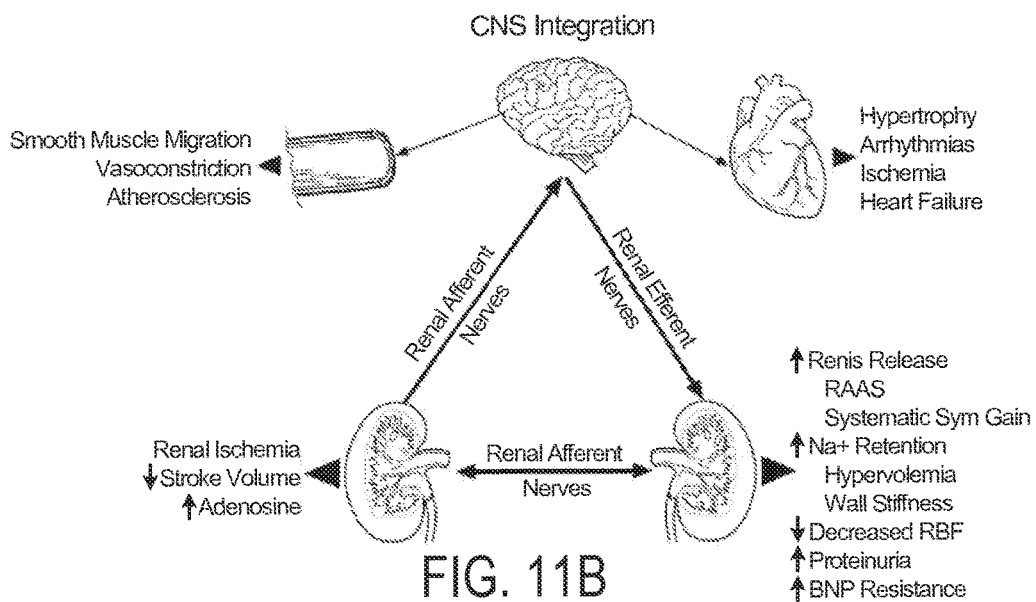

The kidneys communicate with integral structures in the CNS via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 11B and 11B, this afferent communication might be from the kidney to the brain or might be from one kidney to the other kidney (via the CNS). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic overactivity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, sodium retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal neuromodulation, a desirable reduction of central sympathetic outflow to various other organs such as the heart and the vasculature is anticipated.

B. Additional Clinical Benefits of Renal Neuromodulation

As provided above, selective and/or non-selective renal neuromodulation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal neuromodulation and, in one embodiment, selective afferent renal neuromodulation might also be useful in treating other conditions associated with systemic sympathetic hyperactivity. Accordingly, selective and/or non-selective renal neuromodulation may also benefit other organs and bodily structures having sympathetic nerves, including those identified in FIG. 9. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figures 12A, 12B:
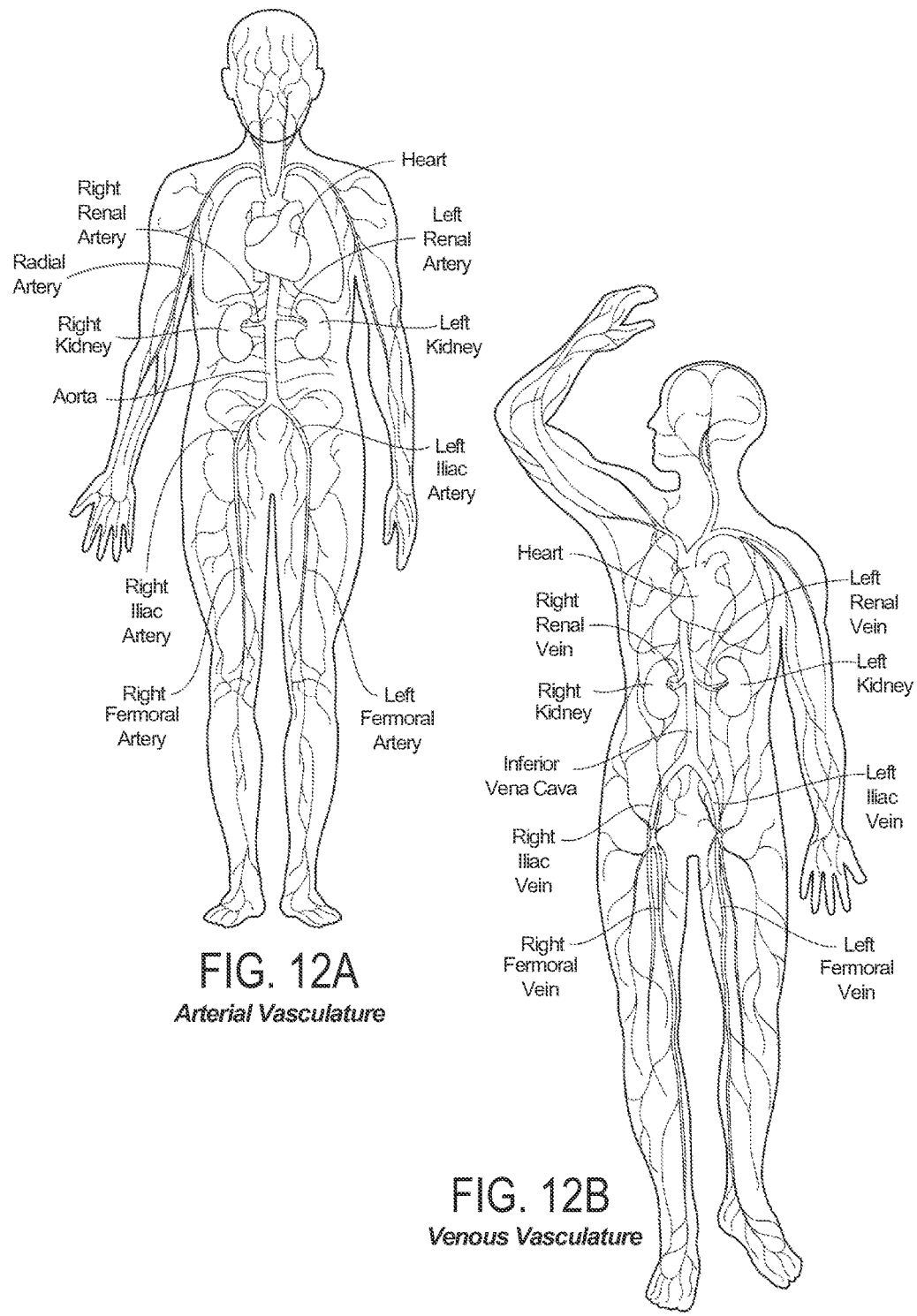
FIGS. 12A and 12B are anatomic views illustrating, respectively, an arterial vasculature and a venous vasculature of a human.

In accordance with the present technology, neuromodulation of a left and/or right renal plexus RP, which is intimately associated with a left and/or right renal artery, may be achieved through intravascular access. As FIG. 12A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 12B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter (not shown) may be inserted percutaneously into the femoral artery through this access site, passed through the iliac artery and aorta, and placed into either the left or right renal artery. This route comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Properties and characteristics of the renal vasculature impose challenges to both access and treatment methods, and to system/device designs. Since neuromodulation of a left and/or right renal plexus RP may be achieved in accordance with embodiments of the present technology through intravascular access, various aspects of the design of apparatus, systems, and methods for achieving such renal neuromodulation are disclosed herein. Aspects of the technology disclosed herein address additional challenges associated with variation of physiological conditions and architecture across the patient population and/or within a specific patient across time, as well as in response to disease states, such as hypertension, chronic kidney disease, vascular disease, end-stage renal disease, insulin resistance, diabetes, metabolic syndrome, etc. For example, the design of the intravascular device and treatment protocols can address not only material/mechanical, spatial, fluid dynamic/hemodynamic and/or thermodynamic properties, but also provide particular algorithms and feedback protocols for delivering energy and obtaining real-time confirmatory results of successfully delivering energy to an intended target location in a patient-specific manner.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery. For example, spiral or helical computed tomography (CT) technology can be used to produce 3D images of the vascular features for individual patients, and intravascular path choice as well as device size/diameter, length, flexibility, torque-ability, kink resistance, etc. can be selected based upon the patient's specific vascular features.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, transducer, heating element or a cryotherapeutic device, consistent positioning and appropriate contact force applied by the energy or cryotherapy delivery element to the vessel wall, and adhesion between the applicator and the vessel wall can be important for predictability. However, navigation can be impeded by the tight space within a renal artery RA, as well as tortuosity of the artery. Furthermore, establishing consistent contact can be complicated by patient movement, respiration, and/or the cardiac cycle because these factors may cause significant movement of the renal artery RA relative to the aorta, and the cardiac cycle may transiently distend the renal artery RA (i.e., cause the wall of the artery to pulse). As mentioned previously, to address these challenges, the treatment device or applicator may be designed with relative sizing and flexibility considerations. For example, the renal artery may have an internal diameter in a range of about 2-10 mm and the treatment device can be delivered using a 3, 4, 5, 6, 7 French, or in some cases, an 8 French sized catheter. To address challenges associated with patient and/or arterial movement during treatment, the treatment device and neuromodulation system can be configured to use sensory feedback, such as impedance and temperature, to detect instability and to alert the operator to reposition the device and/or to temporarily stop treatment. In other embodiments, energy delivery algorithms can be varied in real-time to account for changes detected due to patient and/or arterial movement. In further examples, the treatment device may include one or more modifications or movement resistant enhancements such as atraumatic friction knobs or barbs on an outside surface of the device for resisting movement of the device relative to the desired tissue location, positionable balloons for inflating and holding the device in a consistent and stable position during treatment, or the device can include a cryogenic component that can temporarily freeze or adhere the device to the desired tissue location.

After accessing a renal artery and facilitating stable contact between neuromodulatory apparatus and a luminal surface of the artery, nerves in and around the adventitia of the artery can be modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant (e.g., 1-3 mm) from the luminal surface of the artery. Sufficient energy can be delivered to the target renal nerves to modulate the target renal nerves without excessively cooling or heating the vessel wall to the extent that the wall is frozen, desiccated, or otherwise potentially affected to an undesirable extent. For example, when employing energy modalities such as RF or ultrasound, energy delivery can be focused on a location further from the interior vessel wall. In one embodiment, the majority of the RF or ultrasound energy can be focused on a location (e.g., a "hot spot") 1-3 mm beyond the interior surface of the vessel wall. The energy will dissipate from the hot spot in a radially decreasing manner. Thus, the targeted nerves can be modulated without damage to the luminal surface of the vessel. A potential clinical complication associated with excessive heating is thrombus formation from coagulating blood flowing through the artery. Given that this thrombus may cause a kidney infarct, thereby causing irreversible damage to the kidney, thermal treatment from within the renal artery RA can be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus can also be configured to allow for adjustable positioning and repositioning of an energy delivery element or a cryotherapeutic device, within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery via the cryotherapeutic devices or energy delivery elements and/or repositioning of the neuromodulatory apparatus to multiple treatment locations may be desirable. It should be noted, however, that a benefit of forming a circumferential lesion or ablation may outweigh the potential of renal artery stenosis or the risk may be mitigated with certain embodiments or in certain patients and forming a circumferential lesion or ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging.

Blood flow through a renal artery may be temporarily occluded for a short time with minimal or no complications. However, occlusion for a significant amount of time can be avoided in some cases to prevent injury to the kidney such as ischemia. It can be beneficial to avoid occlusion altogether or, if occlusion is beneficial, to limit the duration of occlusion (e.g., 2-5 minutes).

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the takeoff angle of a renal artery relative to the aorta. These properties will be discussed in greater detail with respect to the renal arteries. However, depending on the apparatus, systems, and methods utilized to achieve renal neuromodulation, such properties of the renal arteries also may guide and/or constrain design characteristics.

As noted above, an apparatus positioned within a renal artery can conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite intima-media thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment can be important to reach the target neural fibers, the treatment typically is not too deep (e.g., the treatment can be less than about 5 mm from the inner wall of the renal artery) so as to avoid non-target tissue and anatomical structures such as the renal vein.

An additional property of the renal artery that may be of interest is the degree of renal motion relative to the aorta, induced by respiration and/or blood flow pulsatility. A patient's kidney, which is located at the distal end of the renal artery, may move as much as four inches cranially with respiratory excursion. This may impart significant motion to the renal artery connecting the aorta and the kidney. Accordingly, the neuromodulatory apparatus can have a unique balance of stiffness and flexibility to maintain contact between a cryo-applicator or another thermal treatment element and the vessel wall during cycles of respiration. Furthermore, the takeoff angle between the renal artery and the aorta may vary significantly between patients, and also may vary dynamically within a patient, e.g., due to kidney motion. The takeoff angle gnerally may be in a range of about 30°-135°.

IX. Examples

Example 1

Effect of Renal Neuromodulation on Hypertension

Patients selected having a baseline systolic blood pressure of 160 mm Hg or more (≥150 mm Hg for patients with type 2 diabetes) and taking three or more antihypertensive drugs, were randomly allocated into two groups: 51 assessed in a control group (antihypertensive drugs only) and 49 assessed in a treated group (undergone renal neuromodulation and antihypertensive drugs).

Patients in both groups were assessed at 6 months. Office-based blood pressure measurements in the treated group were reduced by 32/12 mm Hg (SD 23/11, baseline of 178/96 mm Hg, p<0.0001), whereas they did not differ from baseline in the control group (change of 1/0 mm Hg, baseline of 178/97 mm Hg, p=0.77 systolic and p=0.83 diastolic). Between-group differences in blood pressure at 6 months were 33/11 mm Hg (p<0.0001). At 6 months, 41 (84%) of 49 patients who underwent renal neuromodulation had a reduction in systolic blood pressure of 10 mm Hg or more, compared with 18 (35%) of 51 control patients (p<0.0001).

Example 2

Effect of Renal Neuromodulation on Components of the RAAS in Patients with Resistant Hypertension Eight patients (55.4±13 years) with treatment resistant hypertension were included in a study to determine blood and urine samples levels of individual components of the renin-angiotensin-aldosterone system (RAAS) before (day −1), after (day=1) and again after 3 months of renal nerve ablation.

Results indicated no statistically significant change in renal plasma flow, plasma renin activity or serum angiotensin II levels in this cohort of patients. There was a significant acute decrease in plasma aldosterone concentration one day post ablation (day −1: 161 (140-265) vs. day +1: 110 (101-168) pg/ml, p=0.012) and in accordance an increased urinary sodium/potassium ratio (day −1: 2.41 (1.17-3.44) vs. day +1: 6.02 (4.83-7.92), p=0.028). After 3 months, these changes were no longer evident. Urinary angiotensinogen levels, considered as a parameter of the local renal RAAS activity, tended to be reduced at day +1 (P=0.116) and significantly decreased after 3 months (6.06 (3.02-13.8) vs. 16.6 (8.50-37.0). P=0.046 compared to day −1 levels.

X. Further Examples

1. A method for treating a human patient, comprising:
   selectively neuromodulating afferent renal nerves in the patient compared to efferent renal nerves in the patient; and
   improving a measurable physiological parameter in the patient corresponding to systemic sympathetic overactivity or hyperactivity.

2. The method of example 1, further comprising reducing muscle sympathetic nerve activity at least about 10% in the patient within about three months after selectively neuromodulating the afferent renal nerves.

3. The method of example 1 or example 2, further comprising reducing whole body norepinephrine spillover in the patient.

4. The method of any one of examples 1-3, further comprising reducing whole body norepinephrine spillover at least about 20% in the patient within about three months after selectively neuromodulating the afferent renal nerves.

5. A method for treating a human patient having a diagnosed condition or disease associated with systemic sympathetic overactivity, the method comprising:
   activating a medium within a renal pelvis of a kidney of the patient; and
   at least partially inhibiting sympathetic neural activity in nerves proximate the renal pelvis via the medium.

6. The method of example 5 wherein—
   the medium includes a fluid,
   the method further comprises introducing the fluid into the renal pelvis, and
   activating the medium selectively affects afferent renal nerves compared to efferent renal nerves in the patient.

7. The method of example 5 or example 6, further comprising at least partially blocking the ureter to at least partially maintain the medium in the renal pelvis.

8. The method of any one of examples 5-7 wherein activating the medium includes heating the medium to a temperature sufficient to at least partially inhibit sympathetic neural activity in the nerves.

9. The method of example 8 wherein heating the medium includes applying ultrasound energy to the medium.

10. The method of example 8 or example 9 wherein heating the medium includes focusing ultrasound energy in a focal zone within the medium.

11. The method of example 8 or example 9 wherein the medium is selected to preferentially heat in the presence of the ultrasound energy relative to tissue surrounding the renal pelvis.

12. The method of example 8 or example 9 wherein the medium includes a microbubble contrast agent.

13. The method of any one of examples 5-12, further comprising—
   introducing a catheter through a ureter connected to the renal pelvis; and
   positioning a therapeutic element of the catheter within the renal pelvis.

14. The method of example 13, further comprising activating the medium using the therapeutic element.

15. The method of example 13 or example 14 wherein the therapeutic element includes one or more electrodes configured to delivery radiofrequency energy.

16. The method of example 13 or example 14 wherein the therapeutic element includes a cryotherapeutic cooling assembly.

17. The method of example 13 or example 14 wherein the therapeutic element is configured to deliver microwave energy.

18. The method of example 13 or example 14 wherein the therapeutic element is configured to deliver direct heat.

19. The method of any one of examples 13-18, wherein the therapeutic element includes an opening, and wherein activating the medium includes introducing a chemical into the medium via the opening.

20. The method of example 19, wherein the therapeutic element includes an electrode, and wherein activating the medium further comprises activating the electrode to move at least a portion of the chemical into a wall of the renal pelvis by electrophoresis.

21. A method for treating a human patient, comprising:
   focusing ultrasound energy in a focal zone along a renal pelvic wall of a kidney of the patient; and
   at least partially inhibiting sympathetic neural activity in nerves proximate the renal pelvic wall.

22. The method of example 21, further comprising introducing a fluid into the renal pelvis.

23. The method of example 22, further comprising introducing a catheter through a ureter of the patient; and introducing the fluid via the catheter.

24. The method of example 22 or example 23 wherein the fluid includes an epithelial-protective agent.

25. The method of any one of examples 22-24 wherein the fluid includes polyethylene glycol.

26. The method of any one of examples 22-25 wherein the fluid includes a local anesthetic.

27. The method of any one of examples 22-26, further comprising cooling the fluid to at least partially protect an inner portion of an epithelium of the renal pelvic wall.

28. The method of any one of examples 22-27 wherein the fluid includes a visualization medium.

29. The method of example 28, further comprising—
   imaging the renal pelvis; and
   locating the focal zone based at least partially on the imaging.

30. A method for treating a human patient having a diagnosed condition or disease associated with chronic sympathetic overactivity, the method comprising:
   introducing a catheter through a ureter of the patient;
   positioning a therapeutic element of the catheter within a renal pelvis connected to the ureter; and
   at least partially inhibiting sympathetic neural activity in nerves proximate the renal pelvis using the therapeutic element.

31. The method of example 30 wherein the therapeutic element includes one or more electrodes configured to delivery radiofrequency energy.

32. The method of example 30 wherein the therapeutic element includes a cryotherapeutic cooling assembly.

33. The method of example 30 wherein the therapeutic element is configured to deliver microwave energy.

34. The method of example 30 wherein the therapeutic element includes a plurality of electrodes having a bipolar configuration.

35. The method of any one of examples 30-34 wherein the therapeutic element includes an opening, and at least partially inhibiting sympathetic neural activity includes introducing a chemical into a wall of the renal pelvis via the opening.

36. The method of example 35 wherein therapeutic element includes a needle, and wherein the opening is at an end portion of the needle.

37. The method of example 35 or example 36 wherein the chemical is a neurotoxin.

38. The method of any one of examples 35-37 wherein the chemical is guanethidine.

39. The method of any one of examples 30-38, wherein at least partially inhibiting sympathetic neural activity includes—
   contacting a plurality of locations along the renal pelvic wall with the therapeutic element, and
   at least partially inhibiting sympathetic neural activity in nerves proximate the locations, wherein the locations have relatively-high concentrations of afferent renal nerve terminals.

40. A method for treating a human patient having a diagnosed condition or disease associated with systemic sympathetic overactivity or hyperactivity, the method comprising:

intravascularly positioning a neuromodulation assembly adjacent to efferent and afferent renal nerves of the patient; and selectively neuromodulating efferent renal nerves in the patient compared to afferent renal nerves in the patient, wherein selectively neuromodulating the efferent renal nerves improves a measurable physiological parameter in the patient corresponding to the diagnosed condition or disease associated with systemic sympathetic overactivity or hyperactivity of the patient.

41. The method of example 40, further comprising reducing muscle sympathetic nerve activity at least about 10% in the patient within about three months after selectively neuromodulating the afferent renal nerves.

42. The method of example 40 or example 41, further comprising reducing whole body norepinephrine spillover in the patient.

43. The method of any one of examples 40-42, further comprising reducing whole body norepinephrine spillover at least about 20% in the patient within about three months after selectively neuromodulating the afferent renal nerves.

44. The method of any one of examples 40-43 wherein the patient has been diagnosed as having cystinuria.

45. The method of any one of examples 40-44 wherein the patient has been diagnosed as having an increased risk of developing kidney stones relative to the general population.

46. A method for treating a human patient, comprising:
intravascularly positing a therapeutic element at a position within a renal artery or a renal branch artery of a kidney of the patient; and
at least partially inhibiting sympathetic neural activity at a portion of a renal plexus proximate the position using the therapeutic element, wherein—
the renal plexus has a first concentration of afferent renal nerves at a first location proximate an ostium of the renal artery,
the renal plexus has a second concentration of afferent renal nerves at a second location closer to the kidney than the first location,
the second concentration of afferent renal nerves is less than about 50% of the first concentration of afferent renal nerves, and
the position of the therapeutic element is proximate the second location.

47. The method of example 46 wherein the second concentration of afferent renal nerves is less than about 25% of the first concentration of afferent renal nerves.

48. The method of example 46 or example 47 wherein—
the position is a first position within a first renal branch artery, and
the method further comprises—
intravascularly positing the therapeutic element at a second position within a second renal branch artery of the patient, and
at least partially inhibiting sympathetic neural activity at a portion of the renal plexus proximate the second position using the therapeutic element.

XI. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for treating a hypertensive human patient, comprising:
neuromodulating afferent and efferent renal nerves in the patient, wherein neuromodulating includes selectively neuromodulating afferent renal nerves compared to efferent renal nerves in the patient such that a greater percentage of afferent renal nerves are modulated relative to a percentage of modulated efferent renal nerves; and
wherein selectively neuromodulating the afferent renal nerves in the patient improves a measurable physiological parameter corresponding to the hypertension of the patient.

2. The method of claim 1, further comprising reducing muscle sympathetic nerve activity by at least 10% in the patient within three months after selectively neuromodulating the afferent renal nerves.

3. The method of claim 1, further comprising reducing whole body norepinephrine spillover in the patient.

4. The method of claim 1, further comprising reducing whole body norepinephrine spillover by at least 20% in the patient within three months after selectively neuromodulating the afferent renal nerves.

5. A method for treating a human patient with diagnosed hypertension, the method comprising:
transluminally delivering an energy delivery element of a catheter to a renal pelvis of a kidney of the patient;
delivering energy to afferent and efferent renal nerves in the renal pelvis via the energy delivery element such that a greater volume of afferent renal nerves are modulated relative to a volume of efferent renal nerves; and
removing the energy delivery element and catheter from the patient after treatment;
wherein selectively delivering energy to afferent renal nerves in the renal pelvis improves a measurable physiological parameter associated with the hypertension of the patient within three months to 12 months after treatment.

6. The method of claim 5, further comprising reducing muscle sympathetic nerve activity by at least 10% in the patient within three months after selectively delivering energy to the afferent renal nerves.

7. The method of claim 5, further comprising reducing whole body norepinephrine spillover in the patient.

8. The method of claim 5, further comprising reducing whole body norepinephrine spillover by at least 20% in the patient within three months after selectively delivering energy to the afferent renal nerves.

* * * * *